(12) United States Patent
Cheng et al.

(10) Patent No.: US 9,222,090 B2
(45) Date of Patent: Dec. 29, 2015

(54) RNA INTERFERENCE TARGET FOR TREATING AIDS

(75) Inventors: Tong Cheng, Xiamen (CN); Tao Zhang, Xiamen (CN); Yali Zhang, Xiamen (CN); Ji Miao, Xiamen (CN); Jun Zhang, Xiamen (CN); Ningshao Xia, Xiamen (CN)

(73) Assignees: XIAMEN UNIVERSITY, Xiamen, Fujian Province (CN); YANG SHENG TANG COMPANY LIMITED, Haikou, Hainan (CN)

(*) Notice: Subject to any disclaimer, the term of this patent is extended or adjusted under 35 U.S.C. 154(b) by 442 days.

(21) Appl. No.: 13/584,319

(22) Filed: Aug. 13, 2012

(65) Prior Publication Data
US 2012/0301449 A1 Nov. 29, 2012

Related U.S. Application Data

(63) Continuation of application No. 12/602,005, filed as application No. PCT/CN2008/001074 on Jun. 2, 2008, now abandoned.

(30) Foreign Application Priority Data

May 31, 2007 (CN) .......................... 2007 1 0105818

(51) Int. Cl.
*C12N 15/11* (2006.01)
*C12N 15/113* (2010.01)

(52) U.S. Cl.
CPC ........ *C12N 15/1132* (2013.01); *C12N 2310/11* (2013.01); *C12N 2310/12* (2013.01); *C12N 2310/14* (2013.01)

(58) Field of Classification Search
None
See application file for complete search history.

(56) References Cited

U.S. PATENT DOCUMENTS

| 5,474,796 A | 12/1995 | Brennan |
| 2003/0175950 A1 | 9/2003 | McSwiggen |
| 2005/0069929 A1 | 3/2005 | Chestnut et al. |
| 2005/0246794 A1* | 11/2005 | Khvorova et al. ............ 800/286 |

FOREIGN PATENT DOCUMENTS

| WO | 03099298 | 12/2003 |
| WO | 2004029212 | 4/2004 |

OTHER PUBLICATIONS

Li Fuluan et al., "RNA interference technique and its application in anti-HIV studies", Section Virology Foreign Med Sci Dec. 31, 2004, v11(6), pp. 165-167.
International Search Report for Appln. No. PCT/CN2008/001074.

* cited by examiner

*Primary Examiner* — Tracy Vivlemore
*Assistant Examiner* — Kate Poliakova
(74) *Attorney, Agent, or Firm* — Pillsbury Winthrop Shaw Pittman, LLP

(57) ABSTRACT

The RNAi target sequences, which could be used for treating AIDS through targeting HIV. Based on the target sequences, recombinant expression vectors, packaging vectors and cells were constructed, which express siRNA and/or miRNA and/or ribozyme and/or antisense oligonucleotide for targeting HIV. And the applications of said recombinant expression vectors, packaging vectors and cells in preparing medicament for treating AIDS.

20 Claims, 9 Drawing Sheets

RNA INTERFERENCE TARGET FOR TREATING AIDS

CROSS REFERENCE TO RELATED APPLICASTIONS

This is Continuation Application of U.S. patent application Ser. No. 12/602,005, filed on Feb. 24, 2010, which is a U.S. National Phase of PCT/CN2008/001074, filed Jun. 2, 2008, which in turn claims priority to Chinese Patent Application No. 200810105818.X, filed May 31, 2007, the contents of both of which are incorporated herein in their entirety by reference.

FIELD OF THE INVENTION

The present invention relates to molecular biology, cell biology and gene therapy. More specifically, it relates to 32 RNA interference (RNAi) targets which can be used for AIDS treatment, recombinant expression vectors using the targets, and drugs and methods for treating AIDS obtained in a variety of ways using these targets.

BACKGROUND OF THE INVENTION

Acquired Immune Deficiency Syndrome (AIDS) caused by HIV infection is one of most significant health threat faced by the world. Currently, AIDS has almost spread to countries around the world, and resulted in more than 40 million patients suffering from it, and nearly 30 million people were killed by it (WHO, Report on the Global AIDS Epidemic, 2004). In recent years, the spread of AIDS in China is growing rapidly, and the infected people have already amounted to 0.84 million. At present, the treatment of HIV infection is primarily through high-intensity anti-retrovirus therapy, such as through a combined use of inhibitors against viral reverse transcriptase and protease. However, due to the high mutation rate of HIV and its complex pathogenesis, this type of approach could not completely eradicate the virus in vivo. Therefore, there is an urgent need to develop a new method of treatment for dealing with the threat of AIDS.

RNA interference (RNAi) is a mechanism for inhibiting gene expression intracellularly mediated by a double-stranded RNA (dsRNA), and was first proposed in a research on the inhibition of gene expression in nematode in 1998 (Fire A et al., Nature, 1998, 391:806-811). Further research discovered that the RNAi exists widely in higher mammals and almost all eukaryotic organisms, such as fungi, *arabidopsis*, hydra, planarian, *trypanosoma*, zebrafish etc., and is a widely existing and conservative mechanism for inhibiting gene expression, which may play a role in the regulation of gene expression, protection against virus infection and suppression of the activities of transposon and so on (Dylexhoom D M et al., nature molecular biology review, 2003, 4: 457-467). Working mechanism of RNAi has now almost been elucidated: the endogenous or exogenous dsRNA molecules are cleaved into small interfering RNA (siRNA) in the cytoplasm by Dicer belonging to RNase III. Typical siRNA structural characteristics are: a dsRNA that is 19-23 nt in length with its 5' end phosphorylated and its 3' end symmetrically overhanged by 2-3 nt and with hydroxyl. siRNA molecules bind to the protein complex of RNA-inducing silencing complex (RISC), and the RISC has the helicase and endonuclease activities. The siRNA molecule is unwound in the complex, and the antisense strand can match target mRNA according to the principle of base pairing, and guide the RISC binding to it to enzymatically digest the target mRNA at a position 10 nt from the 5' end in the middle of the antisense strand binding region, thereby inhibiting the expression of the target gene. Currently, main methods for obtaining siRNA include: plasmid and recombinant virus vector that can express small hairpin RNA (shRNA), chemical synthesis, in vitro transcription and so on.

At present, RNAi has shown a good application prospect in the research of prevention and treatment of diseases such as viral disease, including AIDS, and tumor. Studies have shown that siRNA targeting the mRNA of HIV-1 can inhibit the replication of HIV-1 and viral gene expression in HIV-1 susceptible cell cultured in vitro (Martinez M A et al., Immunology Trends, 2002, 23: 559-561). Due to the complicated pathogenic mechanism of HIV, its effective treatment requires highly efficient inhibition of viral replication and gene expression. However, due to the different inhibition efficiency of different targets, not all RNA interference targets met the requirement of conventional design are able to inhibit the expression of target genes effectively. Therefore, suitable RNA interference targets having high inhibition efficiency becomes an important factor in successful HIV treatment using RNAi technology. Selection of an appropriate RNA interference target needs comprehensive considerations in structural features, inhibition efficiency, non-human gene homology and so on. Assistant methods available include the following methods that have been put forward presently: siRNA aided designing software, analysis of the molecular structure of RNA, nucleic acid sequence analysis and alignment and experimental experience etc., these also can be verified through particular inhibition experiment.

Development of novel and more effective AIDS treatment methods are expected based on RNA interference technology, and such kind of treatment method requires a RNA interference target that can effectively suppress HIV replication and expression to be provided. The present invention meets this need and provides a RNA interference target, a recombinant expression vector and so on for such purpose.

BRIEF DESCRIPTION OF THE INVENTION

The present invention provides a highly efficient RNA interference target targeting HIV. The RNA interference target can be used to construct an expression plasmid, a recombinant viral vector and a cell which comprises or into which is introduced a nucleic acid sequence encoding the RNA interference target according to the present invention, and the RNA interference target also can be used to obtain a drug for AIDS treatment comprising the RNA interference target according to the present invention. In a particular aspect of the present invention, it relates to a RNA interference target sequence targeting the HIV GAG, POL, VIF, or VPU gene.

The RNA interference target provided by the present invention can target HIV efficiently, inhibit HIV replication and viral gene expression efficiently. The RNA interference target provided by the present invention is obtained through a method comprising: selecting and designing a RNA interference target sequence that can target HIV, constructing shRNA through designing appropriate primers, and cloning the shRNA into a pSUPER vector to obtain a corresponding shRNA expression plasmid, co-transfecting with the plasinid and a HIV infectious cloning plasmid, and screening for a highly effective RNA interference target by analysis such as detection of the expression level of HIV p24 protein and identification of inhibition specificity.

The present invention provides RNA interference target sequence specifically targeting HIV, said sequence being selected from:

(1) a sequence shown in any one of SEQ ID NO: 1-32, or
(2) a sequence that has at least 70%, preferably at least 80%, 85%, 90%, 95%, 98% or higher identity to the sequences defined in (1), or
(3) a nucleotide sequence able to hybridize with the sequence defined in (1) under stringent conditions or highly stringent conditions, or
(4) a sequence that has only 1-3, preferably 1-2, more preferably 1 different nucleotides from the sequence defined in (1), or
(5) a fragment or complementary sequence of the above sequences.

In a particular aspect of the present invention, the RNA interference target sequence may target to the HIV GAG, POL, VIF, or VPU gene.

The RNA interference targets provided in the present invention may be DNA or RNA sequences.

In a preferred embodiment, the RNA interference targets are selected from siVIF037 (SEQ ID NO:24), siPOL1102 (SEQ ID NO:8), siPOL1217 (SEQ ID NO:10), siPOL1327 (SEQ ID NO:29), and siPOL2252 (SEQ ID NO:22).

The present invention also provided a nucleic acid construct or vector, such as expression vector, which contains the RNA interference target sequence.

The present invention also provided a siRNA or a miRNA, or a ribozyme, or an antisense oligonucleotide, which is obtained from the above-mentioned RNA interference target sequence and can inhibit the expression of the HIV corresponding gene and/or replication and/or infection of HIV.

The present invention also provided a modified recombinant expression vector, which can be used to express the HIV-targeting siRNA and/or miRNA and/or ribozymes and/or anti-sense oligonucleotide of the present invention.

In one embodiment, the recombinant expression vector of the present invention is characterized in that it comprises a nucleic acid sequence encoding the siRNA and/or the miRNA and/or the ribozymes and/or the anti-sense oligonucleotide of the RNA interference target sequence provided by the present invention, wherein the nucleic acid sequence is operably linked with the expression controlling sequence, making it possible to express the siRNA and/or the miRNA and/or the ribozymes and/or the anti-sense oligonucleotide targeting HIV in animal cells (especially mammalian cells, such as human cells, HIV receptor cells, preferably CD4+cells, such as mammalian stem cells, preferably hematopoietic stem cells).

The recombinant expression vector according to the present invention may be a plasmid vector or a viral vector, for example, a retrovirus vector, including a lentivirus vector. Preferably, the recombinant expression vector is a retrovirus vector, more preferably a lentivirus vector.

The present invention provided a modified packaging vector (such as a packaging plasmid) used for the production of a retrovirus vector (for example, a lentivirus vector), which contains a mutated HIV-derived gene sequence(s) used for expressing a packaging protein(s). Specifically, the modified gene sequence(s) can be characterized, independently from one another, in that, the packaging vectors are mutated as follows:

a packaging vector: (SEQ ID NO: 24)
‑‑‑‑‑‑‑‑GTAGACAGGATGAGGATTA‑‑‑‑‑‑‑‑ is mutated to: (SEQ ID NO: 33)
‑‑‑‑‑‑‑‑GTAGACAGGACGAAGATTA‑‑‑‑‑‑‑‑, a packaging vector: (SEQ ID NO: 8)
‑‑‑‑‑‑‑‑GGATTTACCACACCAGACA‑‑‑‑‑‑‑‑ is mutated to: (SEQ ID NO: 34)
‑‑‑‑‑‑‑‑GGATTTACCACCCCCGACA‑‑‑‑‑‑‑‑, a packaging vector: (SEQ ID NO: 10)
‑‑‑‑‑‑‑‑GCTGGACTGTCAATGACAT‑‑‑‑‑‑‑‑ is mutated to: (SEQ ID NO: 35)
‑‑‑‑‑‑‑‑GCTGGACTGTGAACGACAT‑‑‑‑‑‑‑‑, a packaging vector: (SEQ ID NO: 29)
‑‑‑‑‑‑‑‑GCACTAACAGAAGTAGTAC‑‑‑‑‑‑‑‑ is mutated to: (SEQ ID NO: 36)
‑‑‑‑‑‑‑‑GCACTAACAGAAGTGGTGC‑‑‑‑‑‑‑‑,
and a Packaging vector: (SEQ ID NO: 22)
‑‑‑‑‑‑‑‑TAGTAGCCAGCTGTGATAA‑‑‑‑‑‑‑‑ is mutated to: (SEQ ID NO: 37)
‑‑‑‑‑‑‑‑TAGTAGCCAGCTGCGACAA‑‑‑‑‑‑‑‑.

The present invention also involves isolated cells, comprising:
(1) the RNA interference target sequence according to the present invention, or
(2) a nucleic acid construct or vector, such as expression vector, which contains the RNA interference target sequence according to the present invention.

The present invention also involves an isolated cell transformed or transfected or transduced with a recombinant expression vector which can express the siRNA and/or the miRNA and/or the ribozyme, and/or the anti-sense oligonucleotide of the present invention targeting HIV.

The present invention also involves an isolated cell transformed or transfected or transduced with or comprises the packaging vector of the present invention (such as a packaging plasmid).

The present invention also involves a tissue and an organism, such as an animal, that contains the above-mentioned cell.

The present invention also involves a modified cell (including an animal cell, such as a mammalian cell, preferably a human cell, preferably a HIV receptor cell and a stem cell, such as a CD4+cell and a CD34+cell), which can express or contain the siRNA or the miRNA or the ribozyme or the antisense oligonucleotide according to the present invention.

The present invention also involves a cell carrying in or outside of its genome the nucleic acid sequence encoding the RNA interference target according to the present invention, including a prokaryotic cell (for example a bacterial cell, such as a E. coli cell) and a eukaryotic cell (such as a fungal cell, an insect cell, a plant cell, an animal cell, preferably a mammalian cell, such as a human cell, preferably a HIV receptor cell and a stem cell, such as a CD4+cell and a CD34+cell), which contains the nucleic acid sequence encoding the RNA interference target according to the present invention, wherein these nucleic acid sequences can be operably linked with the expression controlling sequence, making it possible to express the siRNA and/or the miRNA and/or the ribozyme, and/or the antisense oligonucleotide in the cell.

The present invention also relates to a combination of DNA sequences, which comprises or consists of first DNA sequence encoding a sense RNA segment and a second DNA sequence encoding an antisense RNA segment, wherein the sense RNA segment contains a RNA sequence encoded by the target sequence according to the present invention, and the antisense RNA segment can form a double-stranded RNA with the sense RNA segment, said double-stranded RNA can suppress the expression if HIV gene and/or the replication and/or infection of HIV.

In a preferred embodiment, HIV receptor cells introduced with a shRNA expression element containing a nucleic acid sequence encoding the RNA interference target obtained from the present invention can thus acquire an ability to inhibit HIV replication and viral gene expression.

The present invention also relates to a tissue and an organism, such as an animal, comprising the cell mentioned above. The present invention also relates to a pharmaceutical composition comprising the cell according to the present invention.

In another aspect, the present invention also relates to a method for the preparation of the modified cell according to the present invention, comprising transforming or transfecting or transducing the cell (including an animal cell such as a mammalian cell, preferably a human cell, preferably a HIV receptor cell and a stem cell, such as a CD4+cell and a CD34+cell) with the recombinant expression vectors according to the present invention.

In an embodiment, the method comprises transducing a mammalian cell, preferably a human HIV receptor cell and a stein cell, such as a CD4+cell and a CD34+cell with the recombinant retrovirus vector according to the present invention (for example, a lentivirus vector, such as the lentivirus Lenti-VIF037, etc.).

In the method mentioned above, the cell can be in an isolated (or ex vivo) form, such as a cell isolated from a HIV-infected patient or a normal individual, or in vivo, or a cell strain cultured in vitro.

The present invention also relates to a combination of DNA sequences, which comprises or consists of a first DNA sequence encoding a sense RNA segment and a second DNA sequence encoding an antisense RNA segment, wherein the sense RNA segment contains a RNA sequence encoded by the target sequence according to the present invention, and the antisense RNA segment can form a double-stranded RNA with the sense RNA segment, said double-stranded RNA can suppress the expression of HBV gene and/or the replication and/or infection of HBV.

The present invention also relates to a small interfering RNA (siRNA), comprising a sense RNA segment and an antisense RNA segment, wherein the sense RNA segment contains a RNA sequence encoded by the target sequence according to the present invention, and the antisense RNA segment can form a double-stranded RNA with the sense RNA segment, and said double-stranded RNA can suppress the expression of HIV corresponding gene and/or replication and/or infection of HIV.

The present invention also relates to a use of the siRNA and/or the miRNA and/or the ribozyme and/or the antisense oligonucleotide obtained from the RNA interference target provided by the present invention in the preparation of a drug and/or a pharmaceutical composition for the treatment of HIV infection or HIV patients.

The present invention also relates to a use of the siRNA and/or the miRNA and/or the ribozyme and/or the antisense oligonucleotide obtained from the RNA interference target provided by the present invention in the preparation of a drug and/or a pharmaceutical composition for the suppression of HIV replication or HIV gene expression.

The present invention also relates to a use of the RNA interference target sequence, or the nucleic acid construct or the vector, or the recombinant expression vector according to the present invention in the preparation of a drug for the treatment of HIV infection or HIV patients.

The present invention also relates to a use of the modified cell according to the present invention (including an animal cell, such as a mammalian cell, preferably a human cell, preferably a HIV receptor cell and a hematopoietic stem cell, such as a CD4+cell and a CD34+cell) in the preparation of a drug and/or a pharmaceutical composition for the treatment of HIV infection or HIV patients.

The present invention also relates to a use of the siRNA target sequence according to the present invention in the screening of anti-HIV drugs.

The present invention also relates to a method for the treatment of HIV infection or HIV patients, comprising administering to an individual in need the RNA interference target sequence, the nucleic acid construct or the vector, the recombinant expression vector, the siRNA or the miRNA or the ribozyme or the antisense oligonucleotide or the cell according to the present invention.

The present invention also relates to a use of the vector and the cell according to the present invention for the treatment of HIV infection or HIV patients.

The present invention also relates to a method for the treatment of HIV infection or HIV patients, comprising administering to a patient a therapeutically effective amount of the RNA interference target sequence, the nucleic acid construct or the vector, the siRNA or the miRNA, or the ribozyme, or the antisense oligonucleotide, the expression vector, the cell, or the siRNA according to the present invention.

The present invention also relates to a method for the suppression of HIV replication or HIV gene expression, comprising administering to an individual in need a therapeutically effective amount of the RNA interference target sequence, the nucleic acid construct or the vector, the siRNA or the miRNA, or the ribozyme, or the antisense oligonucleotide, the expression vector, the cell, or the siRNA according to the present invention.

The present invention also relates to the RNA interference target sequence, the nucleic acid construct or the vector, the siRNA or the miRNA, of the ribozyme, or the antisense oligonucleotide, the expression vector, the cell, or the siRNA according to the present invention used for the treatment of HIV infection or HIV patients, or for the suppression of HIV replication or HIV gene expression.

The present invention will be described more specifically with reference to the following figures. From the detailed description below, the above-mentioned aspects and other aspects of the present invention will be obvious.

Figure 2:
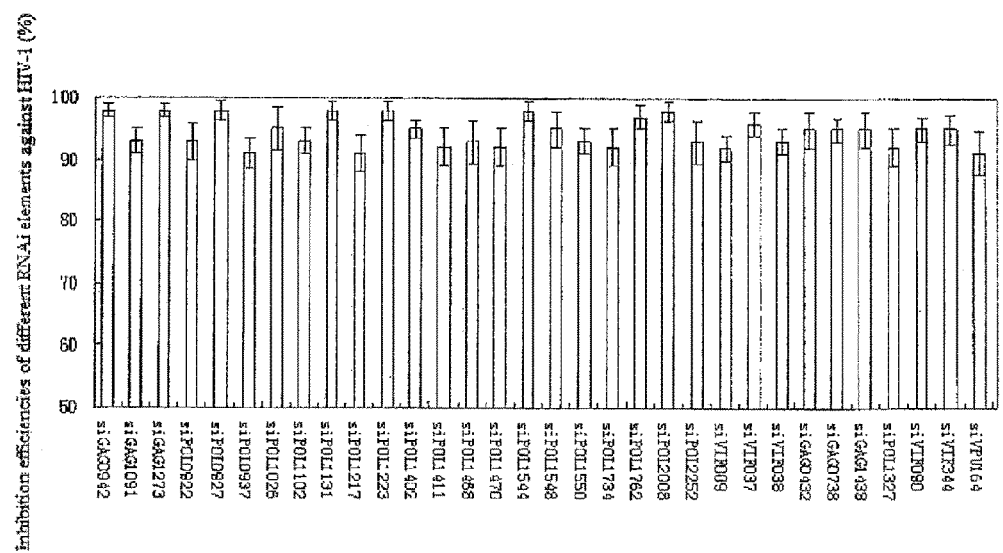

FIG. 2 depicts the suppression effect on HIV gene expression of the siRNA expression plasmids respectively targeting the obtained 32 RNA interference targets in the co-transfection experiment with HIV infectious clone plasmid. The results show that these RNA interference targets can suppress HIV.

Figure 3:
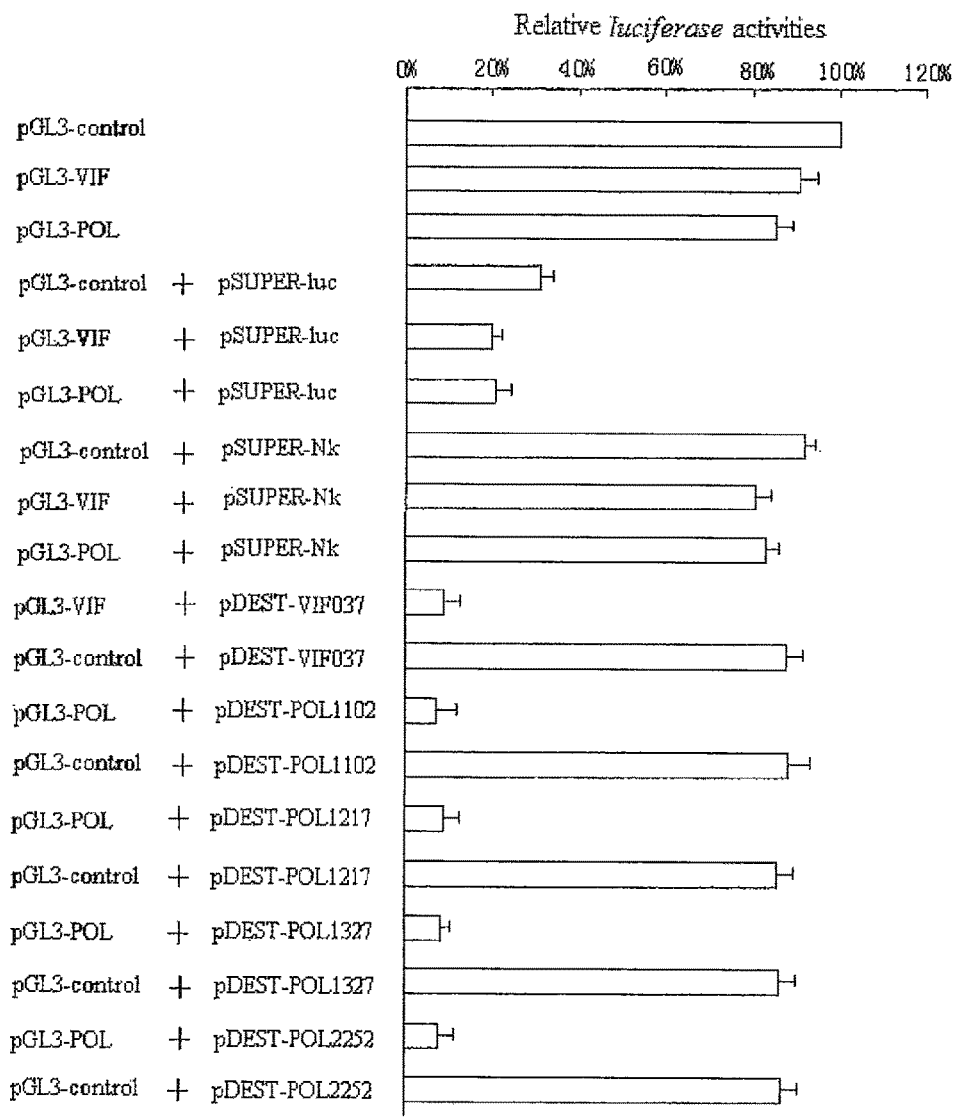

FIG. 3 depicts that the constructed expression vectors pDEST-VIF037, pDEST-POL1102, pDEST-POL1217, pDEST-POL1327, pDEST-POL2252 can effectively express the siRNA sequence encoded, and has the gene targeting specificity. When pGL3-VIF and the expression vector pDEST-VIF037 were co-transfected, the luciferase gene expression was effectively inhibited, while there was no inhibition of luciferase gene expression when pGL3-control and the expression vector pDEST-VIF037 were co-transfected. When pGL3-POL was co-transfected respectively with the expression vectors pDEST-POL1102, pDEST-POL1217, pDEST-POL1327, pDEST-POL2252, the luciferase gene expression was inhibited, while when the pGL3-control was co-transfected respectively with the expression vectors pDEST-POL1102, pDEST-POL1217, pDEST-POL1327, pDEST-POL2252, the luciferase gene expression was not inhibited.

Figure 4:
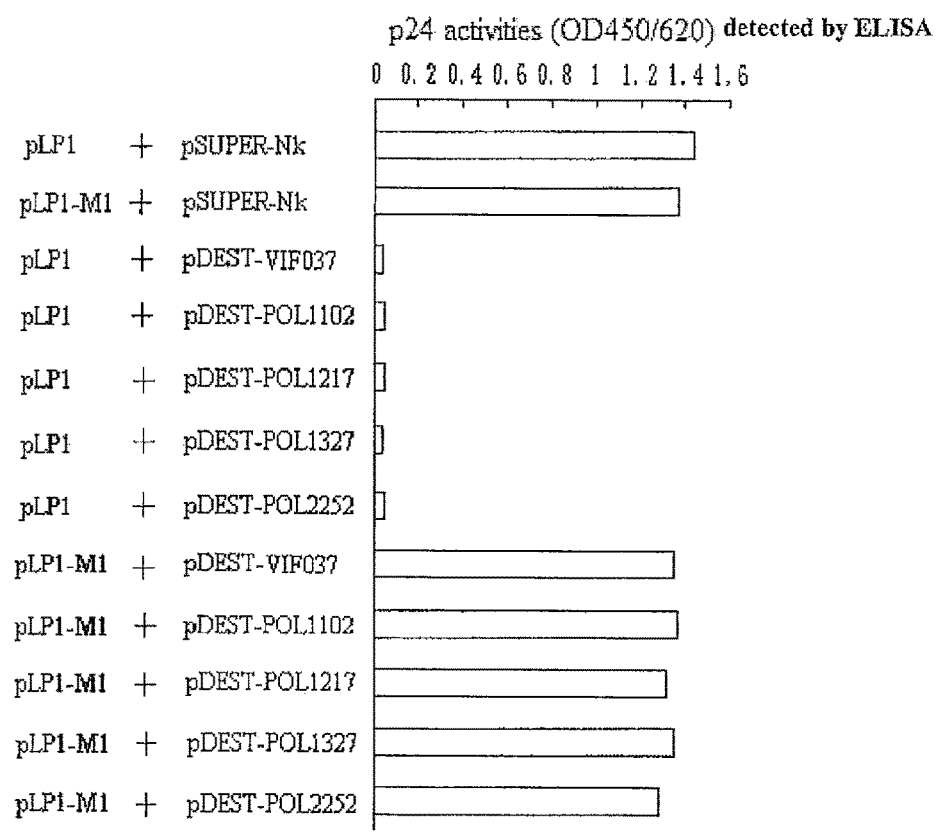

FIG. 4 depicts that the expression of mutated lentivirus packaging vector was not interfered by the lentivirus expression vector expressing the HIV-targeting siRNA.

Figure 5:
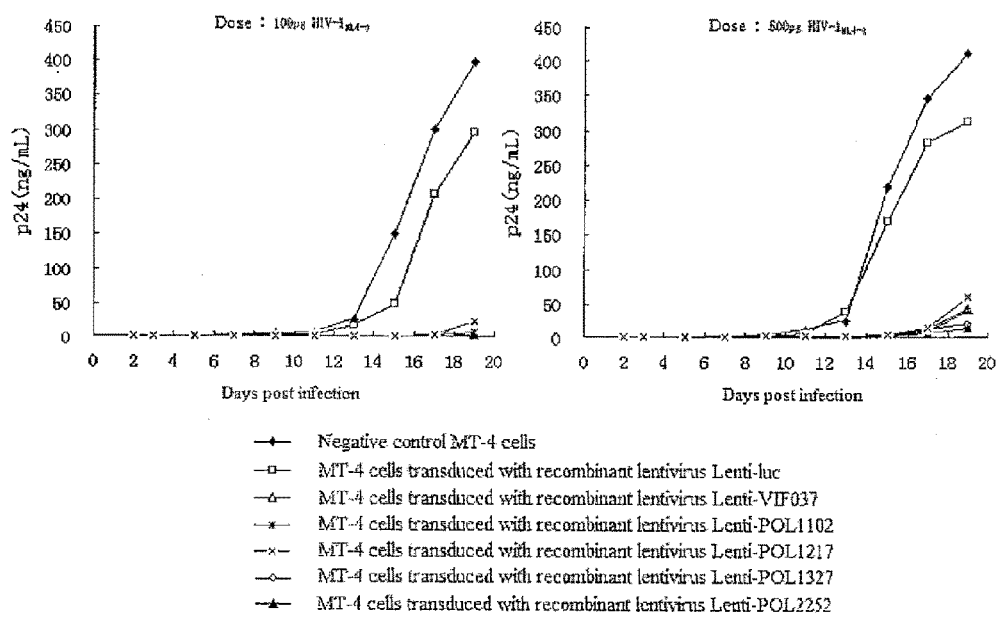

FIG. 5 depicts the inhibitory effect of the HIV receptor cell MT-4 transduced with a recombinant lentivirus carrying HIV-targeting siRNA expression sequences on the replication of HIV-$1_{NL4-3}$.

Figure 6:
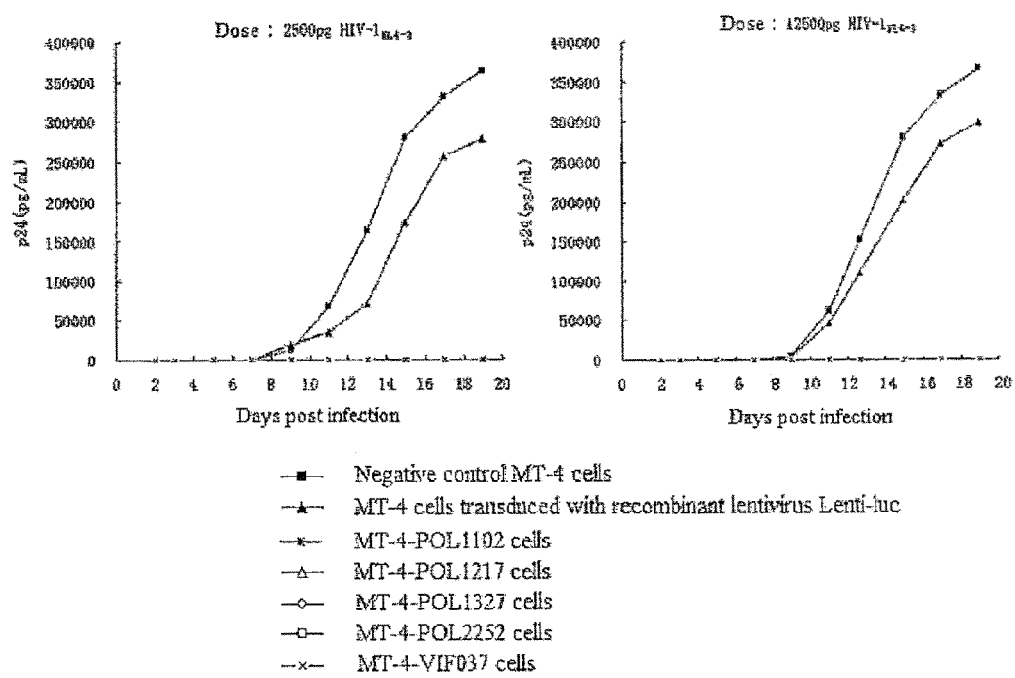

FIG. 6 depicts the inhibitory effect of the mutated HIV receptor cell on the replication of HIV-$1_{NL4-3}$.

Figure 7:
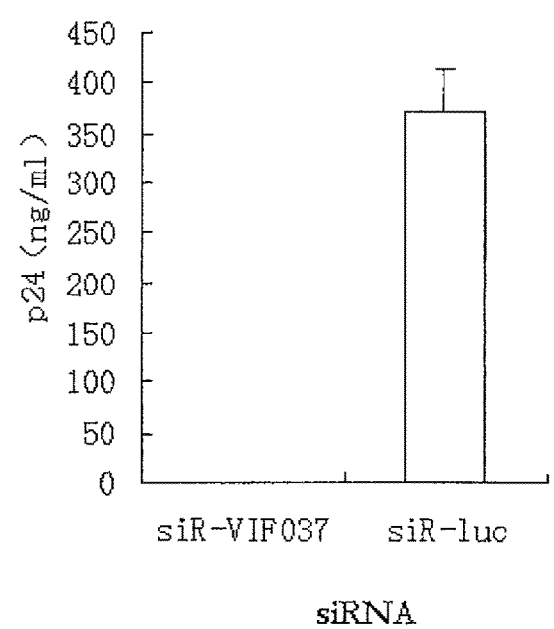

FIG. 7 depicts the inhibitory effect on HIV of the synthesized siRNA of RNA interference target targeting HIV. After transfection, siR-VIF037 can inhibit the replication and expression of HIV in cells.

Figure 8:
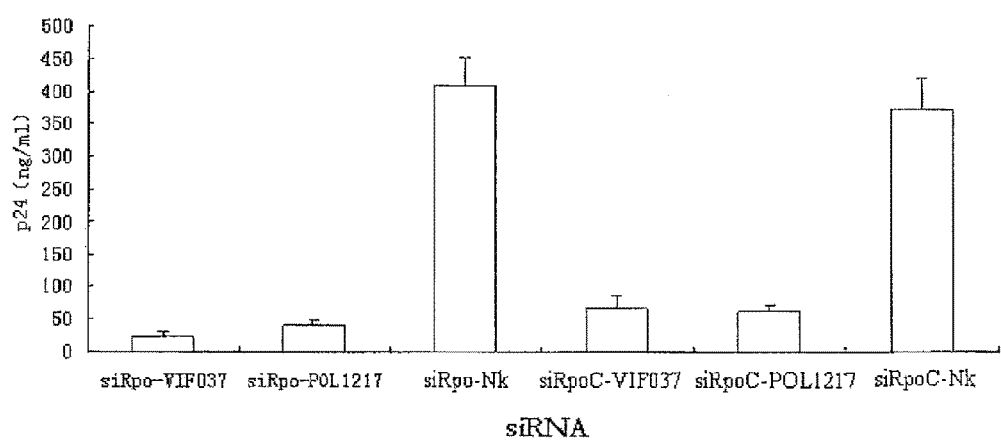

FIG. 8 depicts the inhibitory effect on HIV of the siRNA of RNA interference target targeting HIV. Said siRNA is synthesized and modified by 2'-Ome (2'-methoxy) modification and/or phosphorylation and/or steroid modification. After transfection, siRpo-VIF037, siRpo-POL1217, siRpoC-VIF037, siRpoC-POL1217 can inhibit the replication and expression of HIV in cells.

Figure 9:
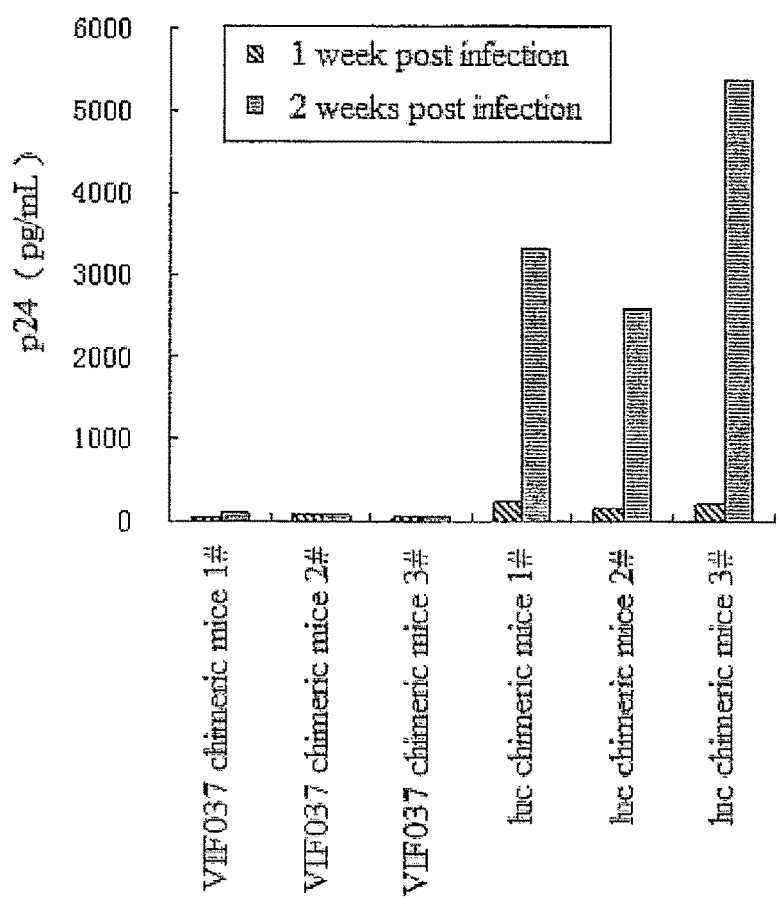

FIG. 9 depicts that the HIV-targeting siRNA has the ability to inhibit the replication of HIV in $H^2K$-PBL-SCID mouse model. VIF037 chimeric mice can show an ability of anti-HIV infection, and can significantly reduce the levels of HIV proteins in the serum comparing to the control group.

DETAILED DESCRIPTION OF THE INVENTION

Unless otherwise stated, the terms of the present invention have the conventional meanings in the art.

The present invention provided a RNA interference target that can target HIV with high efficiency, comprising any one or more sequences shown in SEQ ID NO:1-32 or any one or more sequences that have at least 70% (preferably at least 80%, 85%, 90%, 95%, 98% or higher) identity to the sequences shown in SEQ lD NO:1-32.

The identity can be calculated according to the well-known methods in this art. Preferred examples of algorithms suitable for determining the percentage of sequence identity and sequence similarity are BLAST and BLAST 2.0, which were respectively described in Altschul et al. Nucl, Acid, Res. 1977, Volume 25: page 3389-3402 and Altschul et al. J. MeI, Biol. 1990, Volume 215: page 403-410. Using parameters such as those described herein, BLAST and BLAST 2.0 can be used to determine the percentage of sequence identity of the polynucleotides and polypeptides of the present invention. The software for conducting BLAST analysis can be obtained by the public from the National Center for Biotechnology Information.

In other embodiments, the sequences of the RNA interference target comprise a polynucleotide Sequence that can hybridize with the polynucleotide of the present invention or the fragment or complementary sequence thereof under stringent conditions or highly stringent conditions. Hybridization technology is well-known in the field of molecular biology. For the purpose of illustration, the hybridization condition is a stringent condition, for example, a DNA binding to the filtration membrane is hybridized in 6× sodium chloride/sodium citrate (SSC) at about 45☐, then is washed one or more times in 0.2×SSC/0.1% SDS at about 50-65☐; or is a highly stringent condition, for example, a nucleic acid binding to the filtration membrane is hybridized in 6×SSC at about 45☐, then is washed one or more times in 0.1×SSC/0.2% SDS at about 68☐; or is other stringent hybridization conditions known in the art (See for example, Ausubel, F. M. et al., 1989, Current Protocols in Molecular Biology, Volume 1, Green Publishing Associates, Inc. and John Wiley & Sons, Inc., New York, page 6.3.1-6.3.6 and 2.10.3).

The present invention also relates to a nucleotide sequence which can hybridize with any sequence of SEQ ID NO: 1-32 or the fragment, complementary sequence thereof under stringent conditions or a highly stringent conditions.

According to the present invention, the siRNA and/or the miRNA and/or the ribozyme, and/or the anti-sense oligonucleotide can be designed to target a gene of interest or a regulatory sequence, such as a gene, whose expression is to be inhibited, or a regulatory sequence thereof, in order to inhibit or reduce its expression. The directed gene or the regulatory sequences thereof may be any gene whose expression is to be inhibited or reduced or the regulatory sequence thereof, such as those from the pathogen, or those participating in the formation and development of cancer, and especially those targeting HIV The siRNA, miRNA, ribozyme and antisense oligonucleotide of the present invention can be designed in accordance with conventional methods.

"The siRNA, miRNA, ribozyme and antisense oligonucleotide obtained from the RNA interference target sequence according to the present invention" refers to the siRNA, miRNA, ribozyme and antisense oligonucleotide obtained by ways of designing expression or designing synthesis, and the target sequence (either DNA or RNA sequence) with which they interact is or contains the RNA interference target sequences according to the present invention.

For conventional methods of siRNA design, one can refer to references (such as, Reynolds A et al., Nature Biotechnology, 2004, volume 22: page 326-330) or publicly available information on the web sites of Amhion or Qiagen Inc. etc., or the description in example 1. For conventional methods of miRNA design, one can refer to the paper of Lo F E, et al, Gene Therapy, 2007, Volume 14: page 1503-1512. The methods for selecting target sequences are similar to the methods for designing siRNA. For example, the designed sense strand comprising the target sequence and the corresponding anti-sense strand can replace other sequences of the pri-microRNA, and this enables the constructed miRNA to prevent the expression of the mRNA comprising the target sequence. For conventional methods of ribozyme design, one can refer to the paper of Haseloff J et al, Nature, 1988, Volume 334: page 585-591. For example, nucleotide sequences complementary to sequences upstream and downstream of the target sequence can be placed upstream and downstream of the conservative core sequence of the ribozyme (such as the hammerhead structure) respectively, so that the constructed ribozyme can cleave the nucleic acids containing the target sequence at the target sequence. For conventional methods of antisense oligonucleotides design, one can refer to the paper of Matveeva O V et al, Nucleic Acid Research, 2003, Volume 31: page 4989-4994.

Promoters used in the present invention can be any promoter suitable for expressing desired genes in cells of interest, and can be constitutive or inducible promoters, and also can be complex promoters, such as dual promoters.

"Operably linked" means that the way of linking the linked molecules allows to perform the desired functions. For example, the operable linking of an expression-controlling sequence and a gene-coding sequence allows the expression-controlling sequence to control the expression of the gene-coding sequence.

"Expression controlling sequences" is known to the art as controlling sequences required for gene expression, and it generally must comprise a promoter, and often also comprises a transcription termination sequence, and can also comprise other sequences, such as an enhancer sequence. For the siRNA, miRNA, ribozyme and antisense oligonucleotide etc., gene expression refers to transcription, and can also include post-transcriptional processing; and for protein-coding sequences, it usually refers to transcription and translation, resulting in mature proteins.

The present invention provided a RNA interference target that can highly effectively target HIV and the siRNA, miRNA, ribozyme and antisense oligonucleotide designed according to the target. The siRNA, miRNA, ribozyme and antisense oligonucleotide according to the present invention comprise modified products produced by chemically modifying the constitution moieties, such as phosphate backbone and/or ribose and/or base etc., of the siRNA, miRNA, ribozyme and antisense oligonucleotide. The modification methods are known in the art, which can be thio-modification and/or sterol modification and/or PEG-modification and/or glyco-modification and/or LNA-modification etc. One can refer to, such as Dykxhoorn D M et al, Annual Review of Biomedical Engineering, 2006, Volume 8: page 377-402 and Behlke M A et al, Molecular Therapy, 2006, Volume 13: page 644-670.

In a particular embodiment, the present invention relates to a small interfere RNA (siRNA) comprising a sense RNA segment and an antisense RNA segment, the sense RNA segment contains a RNA sequence encoded by the RNA interfere target according to the present invention, the antisense RNA segment can form a double-stranded RNA with the sense RNA segment and the double-stranded RNA can suppress the expression of HIV corresponding gene and/or the replication and/or infection of HIV.

According to the present invention, the terms "small molecule RNA", "small interfering RNA" or "siRNA" can be used interchangeably, which all refer to RNAs that can suppress the expression of the target HIV gene and contain sense RNA segment region and antisense RNA segment region.

Related, the present invention also provided a combination of DNA sequences which comprises or consists of a first DNA sequence encoding the sense RNA segment and a second DNA sequence encoding the antisense RNA segment, wherein the sense RNA segment comprises a RNA sequence encoded by the target sequence of the present invention, and the antisense RNA segment can form a double-stranded RNA with the sense RNA segment, and the double-stranded RNA can suppress (by RNA interference) the expression of HIV gene and/or the replication and/or infection of HIV.

In such aspect of the present invention, the sense RNA segment and antisense RNA segment could reside in two different RNA strands or a single RNA strand, for example, in one single strand comprising the sense RNA segment and the antisense RNA segment.

For example, the siRNA according to the present invention can be a hairpin single-stranded RNA molecule, wherein a double-stranded RNA region is formed between the complementary regions of the sense RNA segment and the antisense RNA segment.

The length of the sense RNA segment and the antisense RNA segment is preferably 8-50 nt, preferably 10-30 nt (more preferably 15-27nt, 19-23 nt, such as 19 nt, 20 nt or 21 nt). But it could also be longer or shorter.

The complementary region in the double-stranded RNA formed between the sense RNA segment and the antisense RNA segment has at least 10 bp (preferably 15 bp, more preferably 18 bp, e.g. 19 bp, 20 bp or 21 bp). Preferably, the complementary region between the sense RNA segment and the antisense RNA segment comprises 19, 20 or 21 complementary base pairs.

In an embodiment, few bases of mismatch, such as 1-5, e.g. 1 or 2 or 3 or 4 mismatches are allowed to exist between the sense RNA segment and the antisense RNA segment. In a preferred embodiment, the sense RNA segment and the antis ense RNA segment match perfectly.

In an embodiment, the siRNA according to the present invention is a double-stranded RNA molecule with 10-30 bp, preferably 15-27 bp, more preferably 19-23 bp. There are at least 10, preferably 15, more preferably 18 pairs of complementary bases in the double-stranded RNA.

In a preferred embodiment, the GC content of the sense RNA segment and the antisense RNA segment is 35-75%, for example 40-60%, 45-55%, 48-52%, e.g. about 50%.

In a preferred embodiment, there is no significant identity between the sense and antisense RNA segment and a known human gene and the expression fragment of the gene. The significant identity means that there is at least 60%, such as 70%, 80%, 90% identity, Preferably, the ratio between the sum of the number of bases guanine (G) and cytosine (C) in the 19 nucleotide sequence from the 5' end and the number of the 19 nucleotides except for TT in the 3' end (G/C ratio) is 35% to 75% in the sense RNA segment. There is no significant identity between the antisense RNA segment and its mutant having one-nucleotide-mutation and known human genes and gene expression fragments.

In an embodiment of the recombinant expression vector according to the present invention, the recombinant expression vector according to the present invention comprises a nucleic acid sequence encoding the RNA interference target according to the present invention, these nucleic acid sequences are operably linked with expression controlling sequence, thereby making it possible to express the HIV-targeting siRNA and/or miRNA and/or ribozyme and/or antisense oligonucleotide in an animal cell, especially in a mammalian cell, such as a human cell, e.g. a HIV receptor cell and a stem cell.

Similarly, in the method for preparing the modified cell of the present invention, the modified cell of the invention can be obtained by transforming or transfecting or transducing the cell (including an animal cell, such as a mammalian cell, preferably a human cell, preferably a HIV receptor cell and a stem cell, such as a CD4+cell and a CD34+cell) with an expression vector comprising a nucleic acid sequence encoding the RNA interference target according to the present invention, as long as the cells finally obtained comprise the nucleic acid sequence encoding the RNA interference target according to the present invention.

The modified cell according to the present invention can also be obtained by introducing into the cell the siRNA and/or the miRNA and/or the ribozyme and/or the antisense oligonucleotide obtained from the RNA interference target provided by the present invention, as long as the cells obtained comprise the siRNA and/or the miRNA and/or the ribozyme and/or the antisense oligonucleotide obtained from the RNA interference target according to the present invention.

The recombinant expression vector according to the present invention may either be a plasmid vector or a virus vector, such as a retrovirus vector, including a lentivirus vector. Preferably, the recombinant expression vector is a retrovirus vector, more preferably a lentivirus vector.

The modified cell according to the present invention is preferably a mammalian cell, preferably a human cell, preferably a HIV receptor cell, such as a CD4+cell, preferably a stem cell, especially a hematopoietic stem cell, such as a CD34+cell. The cell carries in or outside of its genome a nucleic acid sequence encoding the RNA interference target according to the present invention, which is operably linked with expression controlling sequence, and thereby can express the siRNA and/or the miRNA and/or the ribozyme and/or the antisense oligonucleotide in the cells.

The recombinant vector and the modified cell according to the present invention can be used to treat HIV infection.

In a particular embodiment, the present invention relates to:
1. RNA interference target sequences targeting HIV:

siGAG0942:
(SEQ ID NO. 1)
AAATTGGATGACAGAAACC, siGAG1091:
(SEQ ID NO. 2)
CTGAAGCAATGAGCCAAGT, siGAG1273:
(SEQ ID NO. 3)
GATTGTACTGAGAGACAGGCT, siPOL0922:
(SEQ ID NO. 4)
TGGAAAGGATCACCAGCAA, siPOL0927:
(SEQ ID NO. 5)
AGGATCACCAGCAATATTC, siPOL0937:
(SEQ ID NO. 6)
GCAATATTCCAGTGTAGCA, siPOL1026:
(SEQ ID NO. 7)
GTATGTAGGATCTGACTTA, siPOL1102:
(SEQ ID NO. 8)
GGATTTACCACACCAGACA, siPOL1131:
(SEQ ID NO. 9)
GAAAGAACCTCCATTCCTT,

-continued siPOL1217:
(SEQ ID NO. 10)
GCTGGACTGTCAATGACAT, siPOL1223:
(SEQ ID NO. 11)
CTGTCAATGACATACAGAA, siPOL1402:
(SEQ ID NO. 12)
CCGGTACATGGAGTGTATT, siPOL1411:
(SEQ ID NO. 13)
GGAGTGTATTATGACCCAT, siPOL1468:
(SEQ ID NO. 14)
GGCCAATGGACATATCAAA, siPOL1470:
(SEQ ID NO. 15)
CCAATGGACATATCAAATT, siPOL1544:
(SEQ ID NO. 16)
CCCACACTAATGATGTGAA, siPOL1548:
(SEQ ID NO. 17)
CACTAATGATGTGAAACAA, siPOL1550:
(SEQ ID NO. 18)
ACACTAATGATGTGAAACAATT, siPOL1734:
(SEQ ID NO. 19)
GAAGTTATGGTACCAGTTA, siPOL1762:
(SEQ ID NO. 20)
CCCATAATAGGAGCAGAAA, siPOL2008:
(SEQ ID NO. 21)
TCAGAGTTAGTCAGTCAAA, siPOL2252:
(SEQ ID NO. 22)
TAGTAGCCAGCTGTGATAA, SiVIF009:
(SEQ ID NO. 23)
CAGATGGCAGGTGATGATT, siVIF037:
(SEQ ID NO. 24)
GTAGACAGGATGAGGATTA, siVIF038:
(SEQ ID NO. 25)
TAGACAGGATGAGGATTAA, siGAG0432:
(SEQ ID NO. 26)
TCAGGCCATATCACCTAGA, siGAG0738:
(SEQ ID NO. 27)
AATAGGATGGATGACACAT, siGAG1438:
(SEQ ID NO. 28)
GGAGCCGATAGACAAGGAA, siPOL1327:
(SEQ ID NO. 29)
GCACTAACAGAAGTAGTAC, -continued siVIF090:
(SEQ ID NO. 30)
TATTTCAAGGAAAGCTAAG, siVIF344:
(SEQ ID NO. 31)
TTTCAGAATCTGCTATAAG, siVPU164:
(SEQ ID NO. 32)
GAGTGAAGGAGAAGTATCA;

2. an expression vector, preferably a lentivirus vector, can be used to modify HIV receptor cell or hematopoietic stem cell:
A. a recombinant lentivirus vector that can express the MGMT (P140K) gene and one or more siRNAs and/or miRNAs, and/or HIV-targeting ribozymes,
B. a modified packaging vector for producing lentivirus vector, such as a packaging plasmid, comprising a mutated HIV-derived gene sequence for expressing a packaging protein,
examples of modified sequences are:

```
                                        (SEQ ID NO: 24)
a packaging vector:
--------GTAGACAGGATGAGGATTA--------

(SEQ ID NO: 33)
is mutated to:
--------GTAGACAGGACGAAGATTA--------, (SEQ ID NO: 8)
a packaging vector:
--------GGATTTACCACACCAGACA--------

(SEQ ID NO: 34)
is mutated to:
--------GGATTTACCACCCCCGACA--------, (SEQ ID NO: 10)
a packaging vector:
--------GCTGGACTGTCAATGACAT--------

(SEQ ID NO: 35)
is mutated to:
--------GCTGGACTGTGAACGACAT--------, (SEQ ID NO: 29)
a packaging vector:
--------GCACTAACAGAAGTAGTAC--------

(SEQ ID NO: 36)
is mutated to:
--------GCACTAACAGAAGTGGTGC--------, and (SEQ ID NO: 22)
a packaging vector:
--------TAGTAGCCAGCTGTGATAA--------

(SEQ ID NO: 37)
is mutated to:
--------TAGTAGCCAGCTGCGACAA--------.
```

The use of the lentivirus in a HIV receptor cell and/or a hematopoietic stem cell,
A. to stably express anti-HIV molecules, for example, a siRNA specifically blocking the replication of HIV in the HIV receptor cell and/or the hematopoietic stem cell, or
B. to prevent the hematopoietic stem cell from being killed by BG/BCNU;
3. a modified cell, such as a HIV receptor cell and a hematopoietic stein cell, which comprises a nucleic acid sequence encoding the RNA interference target according to the present invention and can express the siRNA and/or the miRNA and/or the ribozyme and/or the antisense oligonucleotide; or is introduced with the siRNA and/or the miRNA and/or the ribozyme and/or the antisense oligonucleotide obtained from the RNA interference target according to the present invention.

The sequence of the RNA interference target (SEQ ID NO:1-32).

EXAMPLES

Example 1

Design and Construction of the siRNA Expression Plasmid

Design of the RNA interference target sequence targeting HIV was carried out by:
selecting a highly conservative region for the design of the siRNA sequence by "DNA walking" with HIV reference sequence as a target sequence;
conducting BLAST search in the GenBank with the preliminarily selected siRNA sequence; and
selecting sequences that have three or more different bases from non-targeting sequences as candidate sequences.

Figure 1:
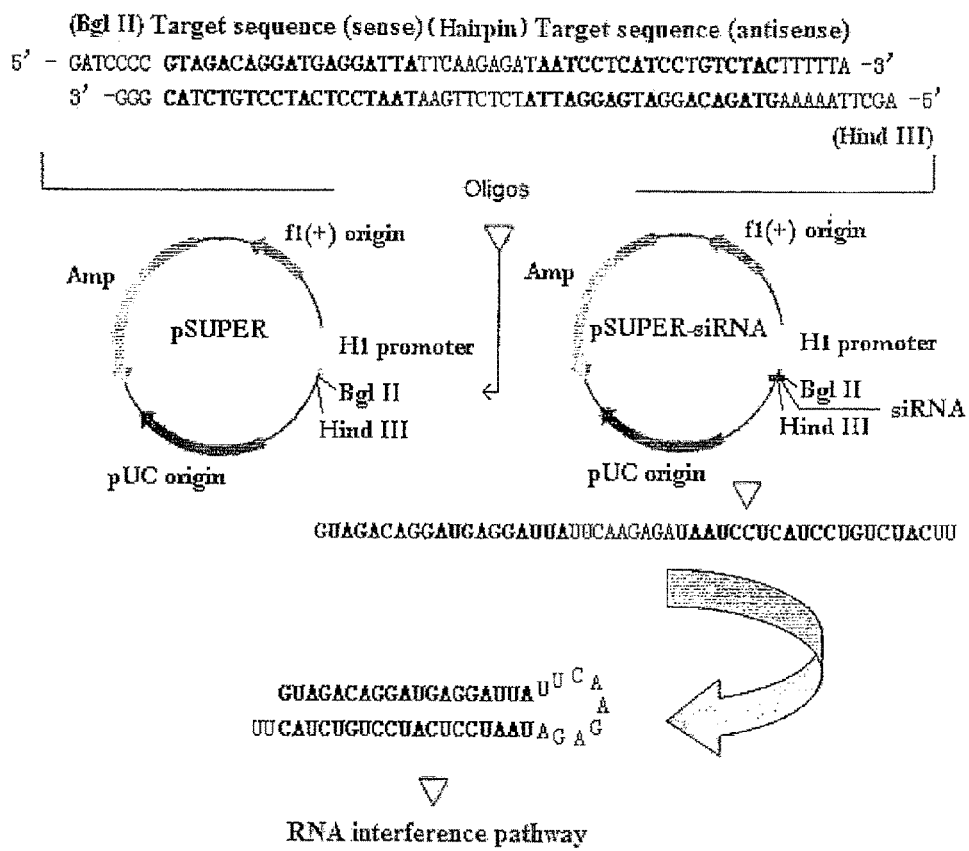
FIG. 1 depicts the flow diagram of the construction of pSUPER-siRNA expression plasmid series, wherein, the sequence 5'-GATCCC GTAGACAGGATGAGGATTA TTCAAGAGA TAATCCTCATCCTGTCTAC TTTTTA-3' is identified as SEQ ID NO: 38; the sequence 5'-AGCT-TAAAAA GTAGACAGGATGAGGATTA TCTCTTGAA TAATCCTCATCCTGTCTAC GGG-3' is identified as SEQ ID NO: 39; the sequence 5'-GUAGACAGGAUGAGGA-UUA UUCAAGAGA UAAUCCUCAUCCUGUCUAC UU-3' is identified as SEQ ID NO: 40.

Construction of the siRNA expression plasmid: the expression vector of the siRNA is pSUPER vector (oligoengine company Cat. No VEC-PBS-0001/0002). For more information about the construction procedure, please refer to Experimental Protocol for the pSUPER vector from the company (www.oligoengine.com). A brief construction procedure is shown in the FIG. 1. Primers carrying the RNA interference sequence were synthesized, complementary primers were annealed and then ligated into the pSUPER vector digested with BglII and HindIII, and the correct siRNA expression plasmid was confirmed by restriction enzyme digestion and sequencing.

Construction of the control siRNA expression plasmid: siRNA-luc (5'-GTGCGCTGCTGGTGCCAAC-3'; SEQ ID NO: 41) which is a siRNA sequence specifically targeting luciferase and siRNA-Nk (5'-TGCATCGGAAAATA-GATGT-3'; SEQ ID NO: 42) which is an unrelated siRNA sequence not matching with HIV and human gene were taken as controls. The synthesis of the primers, construction into the pSUPER vector, obtaining of corresponding siRNA expression plasmid after restriction enzyme digestion and sequencing were carried out using the method described above.

Example 2

Screening by Co-transfection Assay for a RNA Interference Target which can Effectively Inhibiting HIV pNL4-3 plasmid (from Pasteur Institute; may also use other HIV 1 infectious cloning plasmid), a HIV-1 infectious cloning plasmid, has an ability to express HIV viral proteins and viral particles after being transfected into suitable Mammalian cells (for example, 293FT cells). P24 is a capsid protein of the HIV virus, which can indicate the expression level of the virus protein and virus particle by detecting the content of the p24 protein in the supernatant of the cell culture, and is positively correlated with the virus titer. Therefore, the efficiency of different siRNAs in inhibiting the replication of HIV-1 can be determined by co-transfecting the siRNA expression plasmids with HIV infectious cloning plasmid (pNL4-3 plasmid) in the 293FT cells, and detecting the expression level of p24 protein in the cells after co-transfection.

293FT cells (Invitrogen, Catalog #R700-07) were cultured in 24-well cell culture plates to about 70% confluence. After 12 h, cells were transfected with 0.1 μg/well pNIA-3 plasmid and 1 μg/well siRNA expression plasmid, with Lipofectamine 2000 (Invitrogen Cat. No 11668-027) as the transfection reagent. For the method of transfection, see the instructions of the reagent. Cell culture supernatant was collected respectively 48 h after co-transfection, and after gradient dilution, the activity of the p24 protein in the supernatant of the cell culture was examined using Murex HIV Antigen Mab (Cat.No. 8E77-02). The efficiency of each of the siRNAs in inhibiting HIV was calculated using as control the contents of p24 protein in the supernatant of the cell culture of the 293FT cells co-transfected with control siRNA expression plasmid and HIV infectious cloning plasmid. Through comparison, 32 RNA interference targets with the ability of highly effective inhibition were obtained. FIG. 2 shows the inhibitory efficiency of the siRNA expression plasmids constructed respectively with the 32 RNA interference target sequences on HIV viral gene expression after being transfected into the cell.

The RNA interference target sequences that can be used to effectively suppress HIV are listed below:

```
siGAG0942
                            (SEQ ID NO. 1)
AAATTGGATGACAGAAACC siGAG1091
                            (SEQ ID NO. 2)
CTGAAGCAATGAGCCAAGT siGAG1273
                            (SEQ ID NO. 3)
GATTGTACTGAGAGACAGGCT siPOL0922
                            (SEQ ID NO. 4)
TGGAAAGGATCACCAGCAA siPOL0927
                            (SEQ ID NO. 5)
AGGATCACCAGCAATATTC siPOL0937
                            (SEQ ID NO. 6)
GCAATATTCCAGTGTAGCA siPOL1026
                            (SEQ ID NO. 7)
GTATGTAGGATCTGACTTA siPOL1102
                            (SEQ ID NO. 8)
GGATTTACCACACCAGACA siPOL1131
                            (SEQ ID NO. 9)
GAAAGAACCTCCATTCCTT siPOL1217
                            (SEQ ID NO. 10)
GCTGGACTGTCAATGACAT siPOL1223
                            (SEQ ID NO. 11)
CTGTCAATGACATACAGAA siPOL1402
                            (SEQ ID NO. 12)
CCGGTACATGGAGTGTATT siPOL1411
                            (SEQ ID NO. 13)
GGAGTGTATTATGACCCAT siPOL1468
                            (SEQ ID NO. 14)
GGCCAATGGACATATCAAA siPOL1470
                            (SEQ ID NO. 15)
CCAATGGACATATCAAATT siPOL1544
                            (SEQ ID NO. 16)
CCCACACTAATGATGTGAA siPOL1548
                            (SEQ ID NO. 17)
CACTAATGATGTGAAACAA siPOL1550
                            (SEQ ID NO. 18)
ACACTAATGATGTGAAACAATT siPOL1734
                            (SEQ ID NO. 19)
GAAGTTATGGTACCAGTTA siPOL1762
                            (SEQ ID NO. 20)
CCCATAATAGGAGCAGAAA siPOL2008
                            (SEQ ID NO. 21)
TCAGAGTTAGTCAGTCAAA siPOL2252
                            (SEQ ID NO. 22)
TAGTAGCCAGCTGTGATAA siVIF009
                            (SEQ ID NO. 23)
CAGATGGCAGGTGATGATT siVIF037
                            (SEQ ID NO. 24)
GTAGACAGGATGAGGATTA siVIF038
                            (SEQ ID NO. 25)
TAGACAGGATGAGGATTAA siGAG0432
                            (SEQ ID NO. 26)
TCAGGCCATATCACCTAGA siGAG0738
                            (SEQ ID NO. 27)
AATAGGATGGATGACACAT siGAG1438
                            (SEQ ID NO. 28)
GGAGCCGATAGACAAGGAA siPOL1327
                            (SEQ ID NO. 29)
GCACTAACAGAAGTAGTAC siVIF090
                            (SEQ ID NO. 30)
TATTTCAAGGAAAGCTAAG siVIF344
                            (SEQ ID NO. 31)
TTTCAGAATCTGCTATAAG siVPU164
                            (SEQ ID NO. 32)
GAGTGAAGGAGAAGTATCA
```

Through the above experiment, the 32 RNA interference targets according to the present invention were confirmed to be useful in efficiently inhibiting HIV expression.

In the following experiments, siVIF037, siPOL1102, siPOL1217, siPOL1327, siPOL2252 were selected as examples from the RNA interference targets listed above for the further construction of the recombinant lentivirus that can express siRNAs targeting siVIF037, siPOL1102, siPOL1217, siPOL1327, siPOL2252 respectively. For the construction method, see example 3 and example 4.

Example 3

Construction of the Expression Vector and the Lentivirus Packaging Vector Expressing siRNA Expression vector:

The expression vector of the lentivirus system pDEST-MR (patent application number: 200510112917.1; Publication Number: CN1948475) used in this example comprises the MGMT (P140K) gene controlled by the mPGK promoter and an expression cassette for expressing siRNA controlled by the H1 promoter.

Method for Constructing the Expression Vectors pDEST-VIF037, pDEST-POL1102, pDEST-POL1217, pDEST-POL1327, pDEST-POL2252:

Gene fragments VIF037, POL1102, POL1217, POL1327, POL2252 (including as examples the RNA interference target sequences siVIF037 (SEQ ID NO: 24), siPOL1102 (SEQ ID NO: 8), siPOL1217 (SEQ ID NO: 10), siPOL1327 (SEQ ID NO: 29), siPOL2252 (SEQ ID NO: 22) shown in example 2, but may also include other RNA interference target sequences provided by the present invention) were synthesized respectively, and Age I site was added at the 5' end of the fragments, Sma I site was added at the 3' end of the fragments; gene fragments digested with Age I and Sma I were ligated with the plasmid pDEST-MR digested with the same enzymes, thereby constructing the expression vectors pDEST-VIF037, pDEST-POL1102, pDEST-POL1217, pDEST-POL1327, pDEST-POL2252.

The expression effectivity of the constructed recombinant lentivirus expression vectors pDEST-VIF037, pDEST-POL1102, pDEST-POL1217, pDEST_POL1327, pDEST-POL2252 was examined. Reporter plasmids pGL3-VIF and pGL3-POL were constructed by inserting the VIF and POL gene sequence respectively between the stop codon and the PolyA of the luciferase gene in the pGL3-control plasmid (purchased from Promega Corporation). Co-transfection inhibition assay was conducted with the expression plasmid siRNA-luc targeting luciferase and siRNA-Nk targeting unrelated sequences as controls. The results were shown in FIG. 3, when the pGL3-VIF was co-transfected with the expression vector pDEST-VIF037, the expression of the luciferase gene was effectively inhibited, however, when the pGL3-control was co-transfected with the expression vector pDEST-VIF037, the expression of the luciferase gene was not inhibited; and when pGL3-POL was co-transfected with the expression vectors pDEST-POL1102, pDEST-POL1217, pDEST-POL1327, pDEST-POL2252 respectively, the expression of the luciferase gene was effectively inhibited, but when the pGL3-control was co-transfected with the expression vectors pDEST-POL1102, pDEST-POL1217, pDEST-POL1327, pDEST-POL2252 respectively, the expression of the luciferase gene was not inhibited. The results show that the constructed expression vectors pDEST-VIF037, pDEST-POL1102, pDEST-POL1217, pDEST-POL1327, pDEST-POL2252 can express the encoded siRNA sequence, and have gene targeting specificity.

Modification of the Lentivirus Packaging Vector:

Because lentivirus vector is mainly from HIV-1, the in vitro packaging of the lentivirus vector needs several HIV-1 proteins, such as the products of HIV POL and GAG gene. Because it was needed to use lentivirus as an expression vector of the siRNA targeting HIV-1, in order to prevent the siRNA expressed in the expression vector from inhibiting the expression of lentivirus packaging vectors, that is, in order to obtain recombinant lentivirus normally, in this example, corresponding mutations were introduced into the HIV-1-derived gene sequence in the packaging vector. Thus, the mRNA transcribed from the packaging vector in the packaging cells will not be degraded by the siRNA needed to be expressed (for example, the siRNAs selected as examples targeting siVIF037, siPOL1102, siPOL1217, siPOL1327, siPOL2252 respectively in this example).

The mutations of the sequences of the packaging vectors are as follows:

```
                                      (SEQ ID NO: 24)
a packaging vector:
--------GTAGACAGGATGAGGATTA--------

(SEQ ID NO: 33)
is mutated to:
--------GTAGACAGGACGAAGATTA--------, (SEQ ID NO: 8)
a packaging vector:
--------GGATTTACCACACCAGACA--------

(SEQ ID NO: 34)
is mutated to:
--------GGATTTACCACCCCCGACA--------, (SEQ ID NO: 10)
a packaging vector:
--------GCTGGACTGTCAATGACAT--------

(SEQ ID NO: 35)
is mutated to:
--------GCTGGACTGTGAACGACAT--------, (SEQ ID NO: 29)
a packaging vector:
--------GCACTAACAGAAGTAGTAC--------

(SEQ ID NO: 36)
is mutated to:
--------GCACTAACAGAAGTGGTGC--------,
and (SEQ ID NO: 22)
a packaging vector:
--------TAGTAGCCAGCTGTGATAA--------

(SEQ ID NO: 37)
is mutated to:
--------TAGTAGCCAGCTGCGACAA--------.
```

In order to verify whether the expression of the mutated packaging vector will be affected by the siRNA expressed by the expression vector, co-transfection verification assay was conducted, and the results were shown in FIG. 4. The expression of the mutated packaging vector will not be affected by the expression vectors pDEST-VIF037, pDEST-POL1102, pDEST-POLI 217, pDEST-POL1327, PDEST-POL2252,

Example 4

Construction of Recombinant Lentivirus Expressing siRNA and its Efficiency of Gene Transfer for HIV Receptor Cells Apart from the expression vector plasmid expressing the HIV-targeting siRNA and the mutated packaging vector plasmid pLP1-M1, other plasmids needed for the construction of the recombinant lentivirus were pLP2 and VSVG purchased from Invitrogen, with a product name of pLenti4/V5-DEST Gateway Vector Kit, rind a Product Number of No. V469-10.

Method for Preparing the Recombinant Lentivirus:

(1) A large amount of the four plasmids pVSVG, pLP1-M1, pLP2, and expression vector plasmid (such as the exemplary pDEST-VIF037 plasmid, pDEST-POL1102 plasmid, pDEST-POL1217 plasmid, pDEST-POL1327 plasmid, pDEST-POL2252 plasmid in this example) were extracted by cesium chloride-ethidium bromide density gradient centrifugation (for extraction methods, please see "Molecular cloning", J. Sambrook, D W Russell, the Science Press, 2002);

(2) 293FT cells were cultured in DMEM medium (in which 10% FBS, 2 mM L-glutamine, 0.1 mM MEM Non-Essential Amino Acids and 1% penicillin-streptomycin were added);

(3) The 293FT cells were cultured in a cell culture plate with a diameter of 10 cm, to about 70% confluence. After 12 h, co-transfection of the 4 plasmids 10 μg pLP1, 10 μg pLP2, 10 μg pVSVG, and 20 μg expression vector plasmid were mediated by the calcium phosphate transfection method (for the detail of the method, please see "Molecular cloning", J. Sambrook, D W Russell, Science Press, 2002);

(4) The supernatant of the cell culture was collected 48 hours after transfection, and filtrated with a 0.45 μm filtration membrane, and was centrifuged with a SW28 rotor (BECKMAN company) at 25,000 rpm for 90 min at 4 □;

(5) The supernatant was discarded and the precipitate was dissolved with 500 μL PBS;

(6) The virus collecting fluid was aliquoted and stored at −80□ for later use.

MT-4 cells are human-derived CD4+T lymphocytes, which can support the replication of HIV-1. The MT-4 cells were transduced with the recombinant lentiviruses Lenti-VIF037, Lenti-POL1102, Lenti-POL1217, Lenti-POL1327, Lenti-POL2252 respectively with moi=40, and the expression efficiency of the MGMT (P140K) gene in the target cells was detected with immunofluorescence staining and flow cytometry after culturing for 1 week (Table 1). The results showed that recombinant lentivirus Lenti-VIF037, Lenti-POL1102, Lenti-POL1217, Lenti-POL1327, Lenti-POL2252 could effectively transduce MT-4 cells.

TABLE 1

| Recombinant lentivirus | Transduction efficiency for MT-4 cells |
| --- | --- |
| Lenti-VIF037 | 65.02% |
| Lenti-POL1102 | 71.21% |
| Lenti-POL1217 | 70.63% |
| Lenti-POL1327 | 62.25% |
| Lenti-POL2252 | 75.18% |

Table 1 shows the transduction efficiency of recombinant lentiviruses for the CD4+HIV receptor cell MT-4.

Example 5

HIV Inhibition Effect of the HIV-Targeting siRNA Introduced into the HIV Receptor Cells by Recombinant Lentivirus The inhibitory effect of siRNA on HIV was confirmed using a HIV in vitro cell infection model.

MT-4 cell, which is a human-derived CD4+T lymphocyte strain, can support the infection and replication of HIV, and can also be used for the in vitro culture of HIV.

HIV-1$_{NL4-5}$ is a B subtype, T cell-philic HIV-1 virus, which can effectively infect MT-4 cells and replicate therein.

Challenge Test:

MT-4 cells were transduced with lentiviruses Lenti-VIF037, Lenti-POL1102, Lenti-POL1217, Lenti-POL1327, Lenti-POL2252 respectively with moi=40, and the medium was changed after centrifuging at 600 g for 60 min; the MT-4 cells were transduced with control recombinant lentivirus Lenti-luc carrying siRNA expression element targeting luciferase gene (the sequence of the siRNA expression element targeting luciferase gene was the same as in example 1; the control virus was prepared according to the method in example 3 and example 4) with moi=40, and the medium was changed after centrifuging at 600 g for 60 min; The transduced MT-4 cells were cultured at 37□ for 48 h, and were challenged with different doses of HIV-1$_{NL4-3}$ (100 pg and 500 pg) respectively, the medium was changed 12 h after infection; The supernatant of the cell culture was collected at different time points after infection, and the content of p24 protein in the supernatant of the cell culture was detected using Murex HIV Antigen Mab (Cat. No. 8E77-02) detection kit. The controls in the challenge test were untransduced MT-4 cells and MT-4 cells transduced with the control recombinant lentivirus Lenti-lue, The results were shown in FIG. 5, the MT-4 cells transduced with recombinant lentiviruses Lenti-VIF037, Unti-POL1102, Lenti-POL1217, Lenti-POL1327, Lenti-POL2252 all exhibited the ability to inhibit the replication of HIV-1. This showed that the anti-HIV siRNAs were expressed in the HIV receptor cells transduced with the recombinant lentivirus vector carrying the siRNA expression sequence targeting HIV, which resulted in a resistance to HIV infection.

Example 6

Obtaining of the HIV Receptor Cells which can Stably Express the siRNA Targeting HIV by Modification Clonal selection of the MT-4 cells transduced with the recombinant lentiviruses Lenti-VIF037, Lenti-POL1102, Lenti-POL1217, Lenti-POL1327, Lenti-POL2252 was respectively conducted using limiting dilution. Due to the stable integration ability of the lentivirus vector, the HIV-targeting siRNA expression element sequence and the drug screening gene MGMT (P140K) expression element sequence carried by the lentivirus vector may be integrated into the genome of the target cells. Through screening, the expression efficiency of the MGMT (P140K) gene in the selected cells was detected by immunofluorescense staining and flow cytometry. The results were shown in Table 2, MGMT (P140K) gene expression could be detected in more than 99% of the cells after clonal selection. The modified cells were named MT-4-VIF037 cells, MT-4-POL1102 cells, MT-4-POL1217 cells, MT-4-POL1327 cells, MT-4-POL2252 cells respectively.

TABLE 2

| Cells | Expression Efficiency of the MGMT (P140K) gene |
| --- | --- |
| MT-4-VIF037 | 99.90% |
| MT-4-POL1102 | 99.25% |
| MT-4-POL1217 | 99.92% |
| MT-4-POL1327 | 99.30% |
| MT-4-POL2252 | 99.21% |

Table 2 shows the expression efficiency of the drug screening gene MGMT (P140K) in the modified HIV receptor cells.

Example 7

HIV Inhibition Effect of the Modified HIV Receptor Cells in High Dosage HIV Challenge Test The modified HIV receptor cells that can express HIV-targeting siRNA were subjected to high dosage HIV challenge test. In the test, challenging dosage of HIV-$1_{NL4-3}$ was increased to 2500 pg and 12500 pg respectively. The supernatant of the cell culture was collected respectively at different time points after challenging, and the content of p24 protein in the supernatant of the cell culture was detected with Murex HIV Antigen Mab (Cat. No. 8E77-02) detection kit. The results showed (FIG. 6) that, a significant HIV inhibition effect of the modified HIV receptor cells able to stably express the HIV-targeting siRNA (MT-4-POL1102 cells, MT-4-POL1217 cells, MT-4-POL1327 cells, MT-4-POL2252 cells, MT-4-VIF037 cells in the present experiment) could be obtained comparing to the control cells. The results demonstrated that the modified HIV receptor cells carrying the siRNA expression element targeting HIV had the ability of inhibiting the replication and expression of the HIV virus, and therefore could generate resistance to HIV infection.

Example 8

Inhibitory Effect of the Chemically Synthesized siRNA on HIV

From the RNA interference targets described above, siVIF037 was selected as an example (the RNA interference target sequence siVIF037 (SEQ ID NO.24) shown in example 2 was included herein as an example, but other RNA interference target sequences provided by the present invention can also be included), and a siRNA that can target siVIF037 was synthesized, wherein the sense RNA segment of the siRNA comprises the RNA sequence encoded by the target sequence siVIF037 (SEQ ID NO.24) according to the present invention, and the antisense RNA segment can form a double-stranded RNA with the sense RNA segment (in this example, the antisense strand was perfectly complementary to the sense strand, but a few, such as 1 or 2 or 3 or 4 mismatches can be allowed between the antisense and sense strand), dTdT was added to the 3' ends of the sense RNA segment and the antisense RNA segment respectively. The synthesized siRNA was named as siR-VIF037. The siRNA targeting luciferase gene (siR-lue) (the target sequence of the siR-luc was the same as in example 1) was synthesized as a control with the same method.

The method for synthesizing the siRNA is briefly described below: the sense RNA segment and antisense RNA segment of the siRNA were synthesized respectively by β-acetonitrile-phosphoramidite chemosynthesis with automatic DNA synthesizer, the synthesized sense RNA segment and antisense RNA segment were mixed with equal molar ratio, and the desired siRNA was obtained through denaturation and annealing processes in a PCR amplifier.

Experimental Methods:

293FT cells were cultured in 24-well cell culture plate to about 70% confluence. After 12 h, the cells were transfected with 0.1 μg/well pNL4-3 plasmid and 5 ng/well of the chemically synthesized siRNA, with Lipofectamine 2000 (Invitrogen Cat. No 11668-027) as the transfection reagent, for the transfection method, see the manual of the transfection reagent. The supernatant of the cell culture was collected 48 h after co-transfection, and after gradient dilution, the activity of the p24 protein in the supernatant of the cell culture was detected with Murex HIV Antigen Mab (Cat. No. 8E77-02). The inhibitory efficiency of the siR-VIF037 on HIV was calculated with the p24 protein content in the supernatant of the 293FT cell culture as control, these 293FT cells had been co-transfected with the siR-luc and HIV infectious cloning plasmid.

As shown in FIG. 7, the synthesized siR-VIF037 could inhibit the replication and expression of HIV in the cells.

Example 9

Inhibitory Effect of the Chemically Synthesized and Modified siRNA on HIV

From the RNA interference targets described above, siVIF037 and siPOL1217 were selected as examples (the RNA interference target sequences siVIF037 (SEQ ID NO.24) and siPOL1217 (SEQ ID NO.10) shown in example 2 were included herein as examples, but other RNA interference target sequences provided by the present invention can also be included), siRNAs targeting siVIF037 and siPOL1217 were synthesized respectively, wherein the sense RNA segments of the siRNAs comprise the RNA sequences encoded by the target sequences siVIF037 (SEQ ID NO.24) and siPOL1217 (SEQ ID NO.10) of the present invention, and the antisense RNA segments can form double-stranded RNAs with the sense RNA segments, dTdT was added respectively at the 3' ends of the sense RNA segments and the antisense RNA segments. At the same time, different modifications were used in the synthesis process, wherein siRpo-VIF037 and siRpo-POL1217 are siRNAs targeting siVIF037 and siPOL1217 respectively and were modified by 2'-OMe modification (2'-methoxy modification) and phosphorylation (Method of synthesis: the sense RNA segment and antisense RNA segment of the siRNA were synthesized respectively by β-acetonitrile-phosphoramidite chemosynthesis with automatic DNA synthesizer, wherein the three bases at the 5' end and the three bases before dTdT at the 3' end of the sense RNA segments and antisense RNA segments were synthesized with 2'-OMe modified single-nucleotide, and the terminal base of the 5' end of the antisense RNA segment was subjected to phosphorylation; the synthesized sense RNA segments and antisense RNA segments were mixed with equal molar ratio, and the desired siRNA was obtained through the denaturation and annealing processes in a PCR amplifier); siRpoC-VIF037 and siRpoC-POL1217 are siRNAs targeting siVIF037 and siPOL1217 respectively and they were modified by 2'-OMe modification and phosphorylation and sterol modification (the synthesis method is as above, except that when the sense RNA segment was synthesized, the three bases before dTdT at the 3' end were not subjected to 2'-OMe modification, but a Glass supporter comprising cholesterol-aminocaproic-acid-pyrrolidine linker was used as a synthesis support and the bases before dTdT at the 3' end was linked to cholesterol group through phosphorothioate, the remaining steps were the same as the method described above for synthesizing siRpo-VIF037 and siRpo-POL1217). At the same time, siRNAs (siRpo-Nk and siRpoC-Nk) with the same modifications targeting the unrelated RNA interference target siRNA-Nk (the sequence is the same as in example 1) not matching with HIV and human genes were synthesized as control. The 2'-OMe modification and/or phosphorylation and/or sterol modification made to the synthesized siRNAs targeting the RNA interference target sequences siVIF037 (SEQ ID NO.24) and siPOL1217 (SEQ ID NO:10) shown in example 2 were included herein as examples, but other modifications of different types made to the synthesized siRNA targeting other RNA interference target sequences provided by the present invention can also be included.

Experimental Methods:

293FT cells were cultured in 24-well cell culture plate to about 70% confluence, After 12 h, the cells were transfected with 0.1 µg/well pNL4-3 plasmid and 5 ng/well of the synthesized and modified siRNA, with Lipofectamine 2000 (Invitrogen Cat. No 11668-027) as the transfection reagent, for the transfection method, see the manual of the transfection reagent. The supernatant of the cell culture was collected 48 h after co-transfection, and after gradient dilution, the activity of the p24 protein in the supernatant of the cell culture was detected with Murex HIV Antigen Mah (Cat. No. 8E77-02). The inhibitory efficiency of siRpo-VIF037, siRpo-POL1217, siRpoC-VIF037, siRpoC-POL1217 on HIV was calculated with the p24 protein content in the supernatant of the 293FT cell culture as control, these 293FT cells had been co-transfected with siRpo-Nk, siRpoC-Nk, and pNL4-3 plasmid.

The results are shown in FIG. 8, in which the synthesized siRpo-VIF037, siRpo-POL1217, siRpoC-VIF037, siRpoC-POL1217 all could inhibit the replication and expression of HIV in the cells.

Example 10

Examination of the Inhibitory Effect of the siRNA on HIV in the H$^2$K-PBL-SCID Mouse Model From the RNA interference targets described above, siVIF037 was selected as an example (the RNA interference target sequence siVIF037 (SEQ ID NO.24) shown in example 2 was included herein as an example, but other RNA interference target sequences provided by the present invention can also be included), the plasmid pDEST-H$^2$K-VIF037 having the expression cassette of the H$^2$K gene and an expression cassette able to express the siRNA targeting siVIF037 was constructed based on the lentivirus expression vector plasmid pDEST-MR (see example 3). At the same time, the expression cassette in the plasmid pDEST-H$^2$K-VIF037 expressing the siRNA targeting siVIF037 was further substituted with an expression cassette expressing the siRNA targeting luciferase (with the same target sequence as in example 1), and the pDEST-H$^2$K-luc plasmid was obtained as control. With pDEST-H$^2$K-VIF037 and pDEST-H$^2$K-luc, lentiviruses Lenti-H$^2$K-VIF037 and Lenti-H$^2$K-luc were prepared respectively (see the method in example 4).

40 ml of human whole blood was taken, and PBMC cells were isolated using Ficoll-paque plus (GE Healthcare cat. NO 17-1440-03) (for the method, please see the operation manual), and cultured in the AIM-V medium (GIBCO cat. NO 12055) with the stimulation of PHA for 48 h. Then, the PHA-stimulated PBMC cells were transduced with lentiviruses Lenti-H$^2$K-VIF037 and Lenti-H$^2$K-luc (the method for transduction is the same as in example 5). After transduction, the cells were cultured in AIM-V medium containing IL-2 for another 72 h.

The above cells infected by lentiviruses Lenti-H$^2$K-VIF037 and Lenti-H$^2$K-luc and stably expressing the exogenous marker gene H$^2$K were isolated respectively with the MAcSelect Kk transfected cell selection kit (Miltenyi Biotec cat. NO 130-091-986) (for the method, see the operation manual). The selected positive cells were cultured in the AIM-V medium containing IL-2 for another 96 h.

Severe combined immune deficiency (SCID) mice (sterile grade, 7 to 8 weeks old, the weight was about 16~20 g, three mice per group) were injected intraperitoneally with 0.5 ml paraffin oil 1 week before they were used, and then each mouse was injected intraperitoneally with the PBMC cells ($5 \times 10^5$/g body weight) obtained from the above steps to obtain H$^2$K-PBL-SCID chimeric mice. If the human PBMC cells in the mice were derived from the cells transduced with Lenti-H$^2$K-VIF037, then these mice were named as VIF037 chimeric mice for short; if the human PBMC cells were derived from cells transduced with Lenti-H$^2$K-luc, then these mice were called luc chimeric mice for short, HIV-$1_{NL4-3}$ was injected intraperitoneally into the VIF037 chimeric mice and the luc chimeric mice respectively after 12 h. HIV-$1_{NL4-5}$ is the B subtype, T cell-philic HIV-1 virus. 7d and 14 d after virus infection, 200 µL blood was collected by removing the eyeball, and after gradient dilution, the activity of p24 protein in the supernatant of the cell culture was detected with Murex HIV Antigen Mab (Cat. No. 8E77-02). The activity of the p24 protein in luc chimeric mice was served as the experimental control.

The results were shown in FIG. 9, in which the VIF037 chimeric mice had the ability to inhibit the replication of HIV.

Those skilled in the art should know that although specific embodiments of the invention were described for the purpose of exemplary illustration, various modifications can be made without departing from the spirit and scope of the present invention. Therefore, the scope of the present invention should not be viewed to be limited by the embodiments and examples of the present invention. The scope of the present invention is only limited by the claims attached below. All the documents referred to by the present application are incorporated herein by reference in their entirety.

SEQUENCE LISTING

<110> Xiamen University
<120> RNA Interference Targets for Treating AIDS
<130> IEC080028PCT
<160> 32
<170> PatentIn version 3.2

<210> 1
<211> 19
<212> DNA
<213> Artificial Sequence
<400> 1
aaattggatg acagaaacc                                       19

<210> 2
<211> 19
<212> DNA
<213> Artificial Sequence
<400> 2

SEQUENCE LISTING

```
ctgaagcaat gagccaagt                                          19

<210> 3
<211> 21
<212> DNA
<213> Artificial Sequence
<400> 3
gattgtactg agagacaggc t                                       21

<210> 4
<211> 19
<212> DNA
<213> Artificial Sequence
<400> 4
tggaaaggat caccagcaa                                          19

<210> 5
<211> 19
<212> DNA
<213> Artificial Sequence
<400> 5
aggatcacca gcaatattc                                          19

<210> 6
<211> 19
<212> DNA
<213> Artificial Sequence
<400> 6
gcaatattcc agtgtagca                                          19

<210> 7
<211> 19
<212> DNA
<213> Artificial Sequence
<400> 7
gtatgtagga tctgactta                                          19

<210> 8
<211> 19
<212> DNA
<213> Artificial Sequence
<400> 8
ggatttacca caccagaca                                          19

<210> 9
<211> 19
<212> DNA
<213> Artificial Sequence
<400> 9
gaaagaacct ccattcctt                                          19

<210> 10
<211> 19
<212> DNA
<213> Artificial Sequence
<400> 10
gctggactgt caatgacat                                          19

<210> 11
<211> 19
<212> DNA
<213> Artificial Sequence
<400> 11
ctgtcaatga catacagaa                                          19

<210> 12
<211> 19
<212> DNA
<213> Artificial Sequence
<400> 12
ccggtacatg gagtgtatt                                          19

<210> 13
<211> 19
<212> DNA
<213> Artificial Sequence
<400> 13
ggagtgtatt atgacccat                                          19

<210> 14
<211> 19
<212> DNA
<213> Artificial Sequence
<400> 14
ggccaatgga catatcaaa                                          19

<210> 15
<211> 19
<212> DNA
<213> Artificial Sequence
<400> 15
ccaatggaca tatcaaatt                                          19

<210> 16
<211> 19
<212> DNA
<213> Artificial Sequence
<400> 16
cccacactaa tgatgtgaa                                          19

<210> 17
<211> 19
<212> DNA
<213> Artificial Sequence
<400> 17
cactaatgat gtgaaacaa                                          19

<210> 18
<211> 22
<212> DNA
<213> Artificial Sequence
<400> 18
acactaatga tgtgaaacaa tt                                      22

<210> 19
<211> 19
<212> DNA
<213> Artificial Sequence
<400> 19
gaagttatgg taccagtta                                          19

<210> 20
<211> 19
<212> DNA
<213> Artificial Sequence
<400> 20
cccataatag gagcagaaa                                          19

<210> 21
<211> 19
<212> DNA
<213> Artificial Sequence
<400> 21
tcagagttag tcagtcaaa                                          19

<210> 22
<211> 19
<212> DNA
<213> Artificial Sequence
<400> 22
tagtagccag ctgtgataa                                          19

<210> 23
<211> 19
<212> DNA
<213> Artificial Sequence
<400> 23
cagatggcag gtgatgatt                                          19

<210> 24
<211> 19
<212> DNA
<213> Artificial Sequence
<400> 24
```

SEQUENCE LISTING gtagacagga tgaggatta                    19

<210> 25
<211> 19
<212> DNA
<213> Artificial Sequence
<400> 25
tagacaggat gaggattaa                    19

<210> 26
<211> 19
<212> DNA
<213> Artificial Sequence
<400> 26
tcaggccata tcacctaga                    19

<210> 27
<211> 19
<212> DNA
<213> Artificial Sequence
<400> 27
aataggatgg atgacacat                    19

<210> 28
<211> 19
<212> DNA
<213> Artificial Sequence
<400> 28
ggagccgata gacaaggaa                    19

<210> 29
<211> 19
<212> DNA
<213> Artificial Sequence
<400> 29
gcactaacag aagtagtac                    19

<210> 30
<211> 19
<212> DNA
<213> Artificial Sequence
<400> 30
tatttcaagg aaagctaag                    19

<210> 31
<211> 19
<212> DNA
<213> Artificial Sequence
<400> 31
tttcagaatc tgctataag                    19

<210> 32
<211> 19
<212> DNA
<213> Artificial Sequence
<400> 32
gagtgaagga gaagtatca                    19

---

SEQUENCE LISTING

<160> NUMBER OF SEQ ID NOS: 42

<210> SEQ ID NO 1
<211> LENGTH: 19
<212> TYPE: DNA
<213> ORGANISM: Artificial Sequence
<220> FEATURE:
<223> OTHER INFORMATION: RNA interference target sequence targeting HIV

<400> SEQUENCE: 1
aaattggatg acagaaacc                    19

<210> SEQ ID NO 2
<211> LENGTH: 19
<212> TYPE: DNA
<213> ORGANISM: Artificial Sequence
<220> FEATURE:
<223> OTHER INFORMATION: RNA interference target sequence targeting HIV

<400> SEQUENCE: 2
ctgaagcaat gagccaagt                    19

<210> SEQ ID NO 3
<211> LENGTH: 21
<212> TYPE: DNA
<213> ORGANISM: Artificial Sequence
<220> FEATURE:
<223> OTHER INFORMATION: RNA interference target sequence targeting HIV

<400> SEQUENCE: 3
gattgtactg agagacaggc t                  21

<210> SEQ ID NO 4
<211> LENGTH: 19
<212> TYPE: DNA

```
<213> ORGANISM: Artificial Sequence
<220> FEATURE:
<223> OTHER INFORMATION: RNA interference target sequence targeting HIV

<400> SEQUENCE: 4
tggaaaggat caccagcaa                                                19

<210> SEQ ID NO 5
<211> LENGTH: 19
<212> TYPE: DNA
<213> ORGANISM: Artificial Sequence
<220> FEATURE:
<223> OTHER INFORMATION: RNA interference target sequence targeting HIV

<400> SEQUENCE: 5
aggatcacca gcaatattc                                                19

<210> SEQ ID NO 6
<211> LENGTH: 19
<212> TYPE: DNA
<213> ORGANISM: Artificial Sequence
<220> FEATURE:
<223> OTHER INFORMATION: RNA interference target sequence targeting HIV

<400> SEQUENCE: 6
gcaatattcc agtgtagca                                                19

<210> SEQ ID NO 7
<211> LENGTH: 19
<212> TYPE: DNA
<213> ORGANISM: Artificial Sequence
<220> FEATURE:
<223> OTHER INFORMATION: RNA interference target sequence targeting HIV

<400> SEQUENCE: 7
gtatgtagga tctgactta                                                19

<210> SEQ ID NO 8
<211> LENGTH: 19
<212> TYPE: DNA
<213> ORGANISM: Artificial Sequence
<220> FEATURE:
<223> OTHER INFORMATION: RNA interference target sequence targeting HIV

<400> SEQUENCE: 8
ggatttacca caccagaca                                                19

<210> SEQ ID NO 9
<211> LENGTH: 19
<212> TYPE: DNA
<213> ORGANISM: Artificial Sequence
<220> FEATURE:
<223> OTHER INFORMATION: RNA interference target sequence targeting HIV

<400> SEQUENCE: 9
gaaagaacct ccattcctt                                                19

<210> SEQ ID NO 10
<211> LENGTH: 19
<212> TYPE: DNA
<213> ORGANISM: Artificial Sequence
<220> FEATURE:
<223> OTHER INFORMATION: RNA interference target sequence targeting HIV

<400> SEQUENCE: 10
gctggactgt caatgacat                                                19
```

<210> SEQ ID NO 11
<211> LENGTH: 19
<212> TYPE: DNA
<213> ORGANISM: Artificial Sequence
<220> FEATURE:
<223> OTHER INFORMATION: RNA interference target sequence targeting HIV

<400> SEQUENCE: 11
ctgtcaatga catacagaa                                                19

<210> SEQ ID NO 12
<211> LENGTH: 19
<212> TYPE: DNA
<213> ORGANISM: Artificial Sequence
<220> FEATURE:
<223> OTHER INFORMATION: RNA interference target sequence targeting HIV

<400> SEQUENCE: 12
ccggtacatg gagtgtatt                                                19

<210> SEQ ID NO 13
<211> LENGTH: 19
<212> TYPE: DNA
<213> ORGANISM: Artificial Sequence
<220> FEATURE:
<223> OTHER INFORMATION: RNA interference target sequence targeting HIV

<400> SEQUENCE: 13
ggagtgtatt atgacccat                                                19

<210> SEQ ID NO 14
<211> LENGTH: 19
<212> TYPE: DNA
<213> ORGANISM: Artificial Sequence
<220> FEATURE:
<223> OTHER INFORMATION: RNA interference target sequence targeting HIV

<400> SEQUENCE: 14
ggccaatgga catatcaaa                                                19

<210> SEQ ID NO 15
<211> LENGTH: 19
<212> TYPE: DNA
<213> ORGANISM: Artificial Sequence
<220> FEATURE:
<223> OTHER INFORMATION: RNA interference target sequence targeting HIV

<400> SEQUENCE: 15
ccaatggaca tatcaaatt                                                19

<210> SEQ ID NO 16
<211> LENGTH: 19
<212> TYPE: DNA
<213> ORGANISM: Artificial Sequence
<220> FEATURE:
<223> OTHER INFORMATION: RNA interference target sequence targeting HIV

<400> SEQUENCE: 16
cccacactaa tgatgtgaa                                                19

<210> SEQ ID NO 17
<211> LENGTH: 19
<212> TYPE: DNA
<213> ORGANISM: Artificial Sequence
<220> FEATURE:

<223> OTHER INFORMATION: RNA interference target sequence targeting HIV

<400> SEQUENCE: 17
cactaatgat gtgaaacaa                                                19

<210> SEQ ID NO 18
<211> LENGTH: 22
<212> TYPE: DNA
<213> ORGANISM: Artificial Sequence
<220> FEATURE:
<223> OTHER INFORMATION: RNA interference target sequence targeting HIV

<400> SEQUENCE: 18
acactaatga tgtgaaacaa tt                                            22

<210> SEQ ID NO 19
<211> LENGTH: 19
<212> TYPE: DNA
<213> ORGANISM: Artificial Sequence
<220> FEATURE:
<223> OTHER INFORMATION: RNA interference target sequence targeting HIV

<400> SEQUENCE: 19
gaagttatgg taccagtta                                                19

<210> SEQ ID NO 20
<211> LENGTH: 19
<212> TYPE: DNA
<213> ORGANISM: Artificial Sequence
<220> FEATURE:
<223> OTHER INFORMATION: RNA interference target sequence targeting HIV

<400> SEQUENCE: 20
cccataatag gagcagaaa                                                19

<210> SEQ ID NO 21
<211> LENGTH: 19
<212> TYPE: DNA
<213> ORGANISM: Artificial Sequence
<220> FEATURE:
<223> OTHER INFORMATION: RNA interference target sequence targeting HIV

<400> SEQUENCE: 21
tcagagttag tcagtcaaa                                                19

<210> SEQ ID NO 22
<211> LENGTH: 19
<212> TYPE: DNA
<213> ORGANISM: Artificial Sequence
<220> FEATURE:
<223> OTHER INFORMATION: RNA interference target sequence targeting HIV

<400> SEQUENCE: 22
tagtagccag ctgtgataa                                                19

<210> SEQ ID NO 23
<211> LENGTH: 19
<212> TYPE: DNA
<213> ORGANISM: Artificial Sequence
<220> FEATURE:
<223> OTHER INFORMATION: RNA interference target sequence targeting HIV

<400> SEQUENCE: 23
cagatggcag gtgatgatt                                                19

```
<210> SEQ ID NO 24
<211> LENGTH: 19
<212> TYPE: DNA
<213> ORGANISM: Artificial Sequence
<220> FEATURE:
<223> OTHER INFORMATION: RNA interference target sequence targeting HIV

<400> SEQUENCE: 24
gtagacagga tgaggatta                                               19

<210> SEQ ID NO 25
<211> LENGTH: 19
<212> TYPE: DNA
<213> ORGANISM: Artificial Sequence
<220> FEATURE:
<223> OTHER INFORMATION: RNA interference target sequence targeting HIV

<400> SEQUENCE: 25
tagacaggat gaggattaa                                               19

<210> SEQ ID NO 26
<211> LENGTH: 19
<212> TYPE: DNA
<213> ORGANISM: Artificial Sequence
<220> FEATURE:
<223> OTHER INFORMATION: RNA interference target sequence targeting HIV

<400> SEQUENCE: 26
tcaggccata tcacctaga                                               19

<210> SEQ ID NO 27
<211> LENGTH: 19
<212> TYPE: DNA
<213> ORGANISM: Artificial Sequence
<220> FEATURE:
<223> OTHER INFORMATION: RNA interference target sequence targeting HIV

<400> SEQUENCE: 27
aataggatgg atgacacat                                               19

<210> SEQ ID NO 28
<211> LENGTH: 19
<212> TYPE: DNA
<213> ORGANISM: Artificial Sequence
<220> FEATURE:
<223> OTHER INFORMATION: RNA interference target sequence targeting HIV

<400> SEQUENCE: 28
ggagccgata gacaaggaa                                               19

<210> SEQ ID NO 29
<211> LENGTH: 19
<212> TYPE: DNA
<213> ORGANISM: Artificial Sequence
<220> FEATURE:
<223> OTHER INFORMATION: RNA interference target sequence targeting HIV

<400> SEQUENCE: 29
gcactaacag aagtagtac                                               19

<210> SEQ ID NO 30
<211> LENGTH: 19
<212> TYPE: DNA
<213> ORGANISM: Artificial Sequence
<220> FEATURE:
<223> OTHER INFORMATION: RNA interference target sequence targeting HIV
```

```
<400> SEQUENCE: 30
tatttcaagg aaagctaag                                              19

<210> SEQ ID NO 31
<211> LENGTH: 19
<212> TYPE: DNA
<213> ORGANISM: Artificial Sequence
<220> FEATURE:
<223> OTHER INFORMATION: RNA interference target sequence targeting HIV

<400> SEQUENCE: 31
tttcagaatc tgctataag                                              19

<210> SEQ ID NO 32
<211> LENGTH: 19
<212> TYPE: DNA
<213> ORGANISM: Artificial Sequence
<220> FEATURE:
<223> OTHER INFORMATION: RNA interference target sequence targeting HIV

<400> SEQUENCE: 32
gagtgaagga gaagtatca                                              19

<210> SEQ ID NO 33
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 33
gtagacagga cgaagatta                                              19

<210> SEQ ID NO 34
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 34
ggatttacca cccccgaca                                              19

<210> SEQ ID NO 35
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 35
gctggactgt gaacgacat                                              19

<210> SEQ ID NO 36
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 36
gcactaacag aagtggtgc                                              19

<210> SEQ ID NO 37
<211> LENGTH: 19
```

```
<212> TYPE: DNA
<213> ORGANISM: Artificial Sequence
<220> FEATURE:
<223> OTHER INFORMATION: synthetic oligonucleotide

<400> SEQUENCE: 37
tagtagccag ctgcgacaa                                                      19

<210> SEQ ID NO 38
<211> LENGTH: 60
<212> TYPE: DNA
<213> ORGANISM: Artificial Sequence
<220> FEATURE:
<223> OTHER INFORMATION: synthetic oligonucleotide

<400> SEQUENCE: 38
gatccccgta gacaggatga ggattattca agagataatc ctcatcctgt ctacttttta        60

<210> SEQ ID NO 39
<211> LENGTH: 60
<212> TYPE: DNA
<213> ORGANISM: Artificial Sequence
<220> FEATURE:
<223> OTHER INFORMATION: synthetic oligonucleotide

<400> SEQUENCE: 39
agcttaaaaa gtagacagga tgaggattat ctcttgaata atcctcatcc tgtctacggg        60

<210> SEQ ID NO 40
<211> LENGTH: 49
<212> TYPE: RNA
<213> ORGANISM: Artificial Sequence
<220> FEATURE:
<223> OTHER INFORMATION: synthetic oligonucleotide

<400> SEQUENCE: 40
guagacagga ugaggauuau ucaagagaua auccucaucc ugucuacuu                    49

<210> SEQ ID NO 41
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 41
gtgcgctgct ggtgccaac                                                     19

<210> SEQ ID NO 42
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 42
tgcatcggaa aatagatgt                                                     19
```

The invention claimed is:

1. A vector comprising an RNA interference target sequence targeting HIV, which is selected from: (1) a sequence set forth in any one of SEQ ID NOs: 7-8, or (2) a complementary sequence of the sequence defined in (1).

2. A siRNA or a miRNA or a ribozyme obtained based on an RNA interference target sequence targeting HIV, which can inhibit the expression of the corresponding gene of HIV and/or the replication of HIV and/or the infection of HIV, wherein the RNA interference target sequence is selected from: (1) a sequence set forth in any one of SEQ ID NOs: 7-8, or (2) a complementary sequence of the sequence defined in (1).

3. A recombinant expression vector which can express the siRNA or the miRNA or the ribozyme according to claim 2, or an antisense oligonucleotide obtained based on an RNA interference target sequence targeting HIV, which can inhibit the expression of the corresponding gene of HIV and/or the replication of HIV and/or the infection of HIV, wherein the RNA interference target sequence is selected from: (1) a sequence set forth in any one of SEQ ID NOs: 7-8, or (2) a complementary sequence of the sequence defined in (1).

4. The recombinant expression vector according to claim 3, comprising a nucleic acid sequence encoding the siRNA or the miRNA or the ribozyme or the antisense oligonucleotide targeting HIV, wherein the encoding nucleic acid sequence is operably linked to an expression controlling sequence so that the siRNA or the miRNA or the ribozyme or the antisense oligonucleotide can be expressed in an animal cell.

5. The recombinant expression vector according to claim 3, which is a plasmid vector or a virus vector.

6. An isolated cell transformed or transfected or transduced with the recombinant expression vector according to claim 3.

7. A modified cell, which can express or comprises the siRNA or the miRNA or the ribozyme according to claim 2.

8. The modified cell according to claim 7, which carries in its genome or outside of its genome an encoding nucleic acid sequence comprising an RNA interference target sequence targeting HIV selected from: (1) a sequence set forth in any one of SEQ ID NOs: 7-8, or (2) a complementary sequence of the sequence defined in (1), wherein the encoding nucleic acid sequence is operably linked to an expression-controlling sequence so that the siRNA or the miRNA or the ribozyme can be expressed in the cell.

9. A method for producing an isolated cell, comprising transforming or transfecting or transducing a cell, including an animal cell, such as a mammalian cell, preferably a human cell, preferably a HIV receptor cell and a stem cell, such as a CD4+cell and a CD34+cell, with the recombinant expression vector according to claim 3.

10. A small interference RNA (siRNA) comprising a sense RNA segment and an antisense RNA segment, wherein the sense RNA segment comprises a RNA sequence encoded by a target sequence targeting HIV selected from: (1) a sequence set forth in any one of SEQ ID NOs: 7-8, or (2) a complementary sequence of the sequence defined in (1) and the antisense RNA segment can form a double-stranded RNA with the sense RNA segment, and wherein the double-stranded RNA can suppress the expression of the corresponding gene of HIV and/or the replication of HIV and/or the infection of HIV.

11. A method for treating HIV infection or a HIV patient or inhibiting the replication or gene expression of HIV, comprising administering to a patient a therapeutically effective amount of an RNA interference target sequence targeting HIV, which is selected from: (1) a sequence set forth in any one of SEQ ID NOs: 7-8, or (2) a complementary sequence of the sequence defined in (1).

12. A method for treating HIV infection or a HIV patient or inhibiting the replication or gene expression of HIV, comprising administering to a patient a therapeutically effective amount of:
the nucleic acid vector according to claim 1.

13. A method for treating HIV infection or a HIV patient or inhibiting the replication or gene expression of HIV, comprising administering to a patient a therapeutically effective amount of:
the siRNA or the miRNA or the ribozyme according to claim 2, or an antisense oligonucleotide obtained based on an RNA interference target sequence targeting HIV, which can inhibit the expression of the corresponding gene of HIV and/or the replication of HIV and/or the infection of HIV, wherein the RNA interference target sequence is selected from: (1) a sequence set forth in any one of SEQ ID NOs: 7-8, or (2) a complementary sequence of the sequence defined in (1).

14. A method for treating HIV infection or a HIV patient or inhibiting the replication or gene expression of HIV, comprising administering to a patient a therapeutically effective amount of:
the recombinant expression vector according to claim 3.

15. A method for treating HIV infection or a HIV patient or inhibiting the replication or gene expression of HIV, comprising administering to a patient a therapeutically effective amount of:
the cell according to claims 6.

16. A method for treating HIV infection or a HIV patient or inhibiting the replication or gene expression of HIV, comprising administering to a patient a therapeutically effective amount of:
the cell according to claim 7.

17. A method for treating HIV infection or a HIV patient or inhibiting the replication or gene expression of HIV, comprising administering to a patient a therapeutically effective amount of:
the siRNA according to claim 10.

18. The vector according to claim 1, which is an expression vector.

19. The recombinant expression vector according to claim 3, which is a retrovirus vector.

20. The recombinant expression vector according to claim 3, which is a lentivirus vector.

* * * * *